United States Patent [19]
Ozero

[11] 4,134,797

[45] Jan. 16, 1979

[54] PROCESS FOR RECOVERY OF ETHYLENE OXIDE CONTAINING LOW LEVELS OF ALDEHYDIC IMPURITIES

[75] Inventor: Brian J. Ozero, New York, N.Y.

[73] Assignee: Halcon Research & Development Corporation, New York, N.Y.

[21] Appl. No.: 879,544

[22] Filed: Feb. 21, 1978

[51] Int. Cl.² .................... B01D 3/00; B01D 1/14; C07D 301/32

[52] U.S. Cl. ........................... 203/75; 203/82; 203/98; 203/99; 203/DIG. 19; 260/348.37

[58] Field of Search .............. 203/99, 98, 1, DIG. 19, 203/14, 75, 82, 96, 97, 92, 93, 49; 260/348.37

[56] References Cited

U.S. PATENT DOCUMENTS

| | | | |
|---|---|---|---|
| 2,615,901 | 10/1952 | McClellan | 260/348.37 |
| 3,398,062 | 8/1968 | Tsao | 260/348.37 |
| 3,418,338 | 12/1968 | Gilman et al. | 260/348.37 |
| 3,531,376 | 9/1970 | Minoda et al. | 203/99 |
| 4,008,131 | 2/1977 | Price | 203/99 |

Primary Examiner—Wilbur L. Bascomb, Jr.
Attorney, Agent, or Firm—William C. Long; David Dick; Jack B. Murray, Jr.

[57] ABSTRACT

A process for the recovery of ethylene oxide containing low levels of aldehydic impurities from an impure aqueous ethylene oxide solution containing the same is provided in which the impure solution is treated in a novel multi-stage, countercurrent distillation zone for improved separation of said aldehydic impurities and recovery of an ethylene oxide-containing product stream having the desired low concentration of aldehydic impurities.

31 Claims, 9 Drawing Figures

PROCESS FOR RECOVERY OF ETHYLENE OXIDE CONTAINING LOW LEVELS OF ALDEHYDIC IMPURITIES

BACKGROUND OF THE INVENTION

1. Field of the Invention

This invention relates to the recovery of ethylene oxide from aqueous solutions containing the same and, more specifically, to an improved recovery system in which ethylene oxide is separated from an impure aqueous solution containing aldehydic impurities.

2. Description of the Prior Art

Ethylene oxide, a staple in commerce, is prepared by the industry in large quantities by oxidizing ethylene with air or elemental oxygen over a suitable catalyst, typically a silver-containing catalyst, at elevated temperature (100° C. to 500° C. is typical) and at superatmospheric pressure (2 to 25 atmospheres), e.g., by the process of U.S. Pat. No. 2,775,510.

The dilute ethylene oxide mixtures obtained from these reactions, which may be suitably conducted in fixed or fluid-bed reactors, are scrubbed with water to form an aqueous solution of ethylene oxide and to thereby separate the ethylene oxide from unreacted ethylene, oxygen and other gaseous components of the reaction mixture (e.g., carbon dioxide). The separated gaseous materials are generally recycled to the catalytic oxidation step. The aqueous ethylene oxide solution is withdrawn from the absorber and passed to a stripper, e.g., stripping column. In the stripper, generally steam is introduced, usually countercurrently to the ethylene oxide solution fed thereto, to remove ethylene oxide product as overhead. An aqueous stream containing small quantities of formaldehyde and ethylene oxide is withdrawn from the stripper as bottoms and is recirculated to the absorber for use in absorbing additional ethylene oxide.

The overhead product from the stripping column, containing $CO_2$, ethylene oxide, gaseous inerts and water vapor, is cooled to partially condense the ethylene oxide and water contained therein, and the resulting mixture of vapor and liquid is passed to an ethylene oxide reabsorber, in which the uncondensed ethylene oxide vapor is reabsorbed in water. A predominance of the carbon dioxide and gaseous inerts which remain unabsorbed are readily separated as gaseous overhead stream from this reabsorption step. An aqueous solution is thus obtained which contains the reabsorbed ethylene oxide and aldehydic impurities, such as formaldehyde and acetaldehyde, as well as dissolved carbon dioxide and other gaseous impurities, and which must be further treated to provide the high purity ethylene oxide required by the industry. In the processes of U.S. Pat. Nos. 3,165,539, 3,174,262, and 3,964,980, this aqueous stream is passed to a "refining column" in which ethylene oxide is recovered as overhead and an aqueous bottoms is withdrawn for recycle to the reabsorber. In some processes (e.g., U.S. Pat. No. 3,904,656), the ethylene oxide overhead from the refining column is further purified in a second distillation column to remove any remaining carbon dioxide as overhead, and ethylene oxide bottoms are obtained which are passed to a third distillation column wherein purified ethylene oxide product is recovered as overhead.

While the above methods produce an ethylene oxide which is substantially free of water, carbon dioxide and dissolved inert gases, these methods have not economically dealt with the low concentrations of aldehydic impurities such as formaldehyde and acetaldehyde which are present in the ethylene oxide sought to be purified.

For example, while the prior art has typically removed formaldehyde as an overhead bleed in the purification step following reabsorption of the ethylene oxide from the stripping column, this has several disadvantages. If the formaldehyde concentration in the overhead bleed is high, a solid paraformaldehyde phase can form in the overhead system of the column which can result in blockage and erratic operation and can possibly require shutdown and cleanout. See, e.g., J. Frederic Walker, *Formaldehyde*, pgs. 140–163 (3d Ed. Reinhold Publishing Corp.). On the other hand, if the overhead bleed contains a low formaldehyde concentration, the relative amount of ethylene oxide therein is excessive and this results in yield loss of desired purified material.

While U.S. Pat. No. 3,418,338 offers a process which provides more efficient removal of formaldehyde, the attendant disadvantage of the presence of acetaldehyde is not completely solved by this process, and separation of these aldehydic impurities to provide a more pure ethylene oxide stream without the use of condensation and further distillation required by this process would be advantageous from a cost standpoint.

SUMMARY OF THE INVENTION

According to the process of the present invention, a process for treating impure aqueous ethylene oxide solutions containing as impurity at least one aldehyde selected from the group consisting of formaldehyde and acetaldehyde to provide ethylene oxide substantially free of said aldehydic impurities, is provided which comprises (a) passing said impure solution as a feed stream to a multi-stage countercurrent distillation zone having disposed therewith in ascending order above said feed stream the following fractionation regions:
  (1) a first fractionation region of at least 1 theoretical vapor-liquid contacting stage;
  (2) a second fractionation region of at least 1 theoretical vapor-liquid contacting stage;
  (3) a third fractionation region of at least 5 theoretical vapor-liquid contacting stages; and
  (4) a fourth fractionation region of at least 1 theoretical vapor-liquid contacting stage; said multi-stage, countercurrent distillation zone having disposed therewithin below said feed stream a fifth fractionation region of at least 1 theoretical vapor-liquid contacting stage; each of said fractionation regions having means for providing countercurrent contact between downflowing liquid and upwardly flowing vapor;

(b) introducing stripping vapor to said distillation zone below said fifth fractionation region;

(c) withdrawing from the distillation zone as a first side stream at least a portion of the liquid downflowing from said third fractionation region, said first side stream comprising an acetaldehyde-rich ethylene oxide stream;

(d) withdrawing from the distillation zone as a second side stream at least a portion of the liquid downflowing from said fourth fractionation region, said second side stream comprising ethylene oxide substantially free of aldehydic impurities;

(e) withdrawing formaldehyde-containing vapor from said distillation zone above said fourth fractionation region, condensing at least a portion of said withdrawn vapor and recycling at least a portion of the condensate so produced as liquid reflux to the distillation zone above said fourth fractionation region; said condensate being recycled as reflux to said distillation zone in an amount sufficient to provide an internal liquid reflux ratio of at least about 1.35:1, as defined by the expression $$R = L/P + F$$

wherein R is the internal liquid reflux ratio, L is the moles per hour of liquid downflowing to the third fractionation region from the fourth fractionation region, P is the moles per hour of liquid withdrawn as said second side stream and F is the moles per hour of said withdrawn vapor not so recycled as condensate to the distillation zone; the portion of said condensate not so recycled being withdrawn as formaldehyde-rich, ethylene oxide stream; and (f) withdrawing from the distillation zone a liquid bottoms product comprising an aqueous solution substantially free of ethylene oxide.

Preferably, at least a portion of liquid downflowing from said second fractionation region is withdrawn from the distillation zone as a third side stream and is treated to vaporize at least a portion of said third side stream. The thus-produced side-stream vapor is then reintroduced to the distillation zone between said first and second fractionation regions; the quantity of heat introduced to the distillation zone with said side-stream vapor comprising at least 5% of the total stripping heat supplied to the distillation zones.

The process of the present invention has surprisingly been found to result in rapid and efficient removal of such aldehydic impurities while effecting substantial cost savings in utility costs (e.g., heating and cooling expense), as well as capital equipment expense.

DETAILED DESCRIPTION OF THE INVENTION

Figure 1:
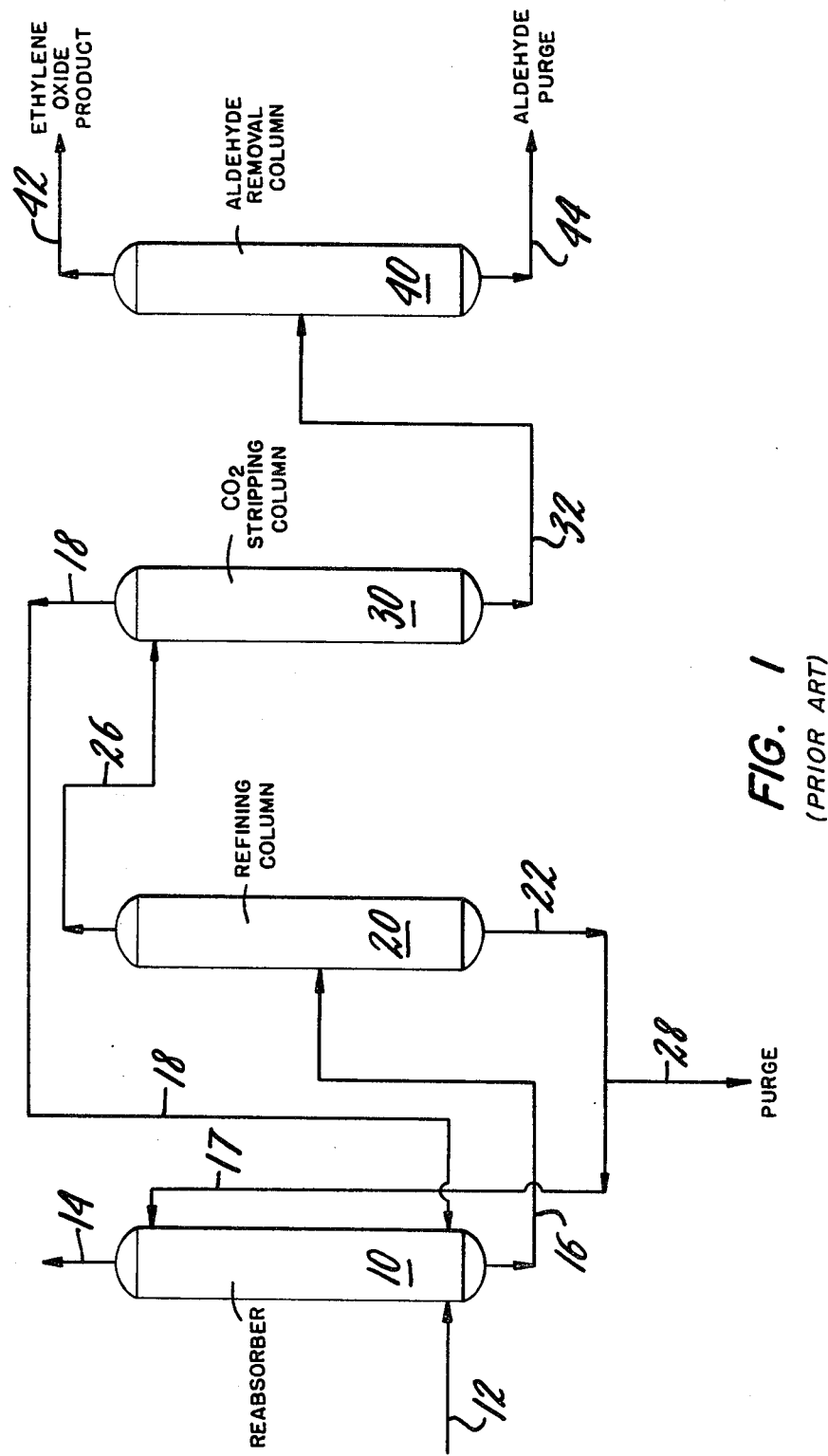
FIG. 1 is a diagrammatic illustration of a typical prior art process for recovery of high-purity ethylene oxide which includes facilities for removal of aldehydic impurities from ethylene oxide streams.

A further understanding of this invention will be facilitated by a reference to the drawings, wherein like numerals refer to the same or similar element. Referring first to FIG. 1, a typical prior art process is illustrated in which an ethylene oxide vapor stream containing carbon dioxide and aldehydic impurities is passed via conduit 12 from a stripper (not shown) to the lower portion of reabsorber 10 wherein it is contacted in countercurrent fashion with an aqueous stream which is introduced to the upper portion of reabsorber 10 via conduit 17. Unabsorbed gases such as carbon dioxide are vented from reabsorber 10 via conduit 14, and bottoms comprising an aqueous solution of reabsorbed ethylene oxide, containing impurities and hereinafter referred to as "reabsorbate", is withdrawn from reabsorber 10 via conduit 16 and passed to refining column 20 wherein ethylene oxide is vaporized and recovered as overhead product (hereinafter referred to as the "refining column overhead") via conduit 26. Aqueous bottoms which are generally substantially free of ethylene oxide are withdrawn via conduit 22 from refining column 20 and recycled via conduit 17 to reabsorber 10, with a portion of the recycled bottoms being withdrawn via conduit 28 to purge water, formaldehyde and ethylene glycol, which is, for example, formed by the hydrolysis of ethylene oxide in refining column 20.

The refining column overhead is passed via conduit 26 to carbon dioxide stripping column 30 wherein residual absorbed gases in the refining column overhead are vaporized and withdrawn via conduit 18 for recycle to reabsorber 10. Vapors withdrawn via conduit 18 are primarily ethylene oxide and $CO_2$, but other gases such as $N_2$, Ar, $CH_4$, $CH_2CH_2$ and $CH_3CH_3$ can also be present. Bottoms withdrawn from column 30 via conduit 32 comprise a crude ethylene oxide solution substantially free of water and $CO_2$ and are passed to purification column 40 for recovery of purified ethylene oxide. An overhead product containing ethylene oxide is withdrawn from column 40 via column 42, and bottoms from column 40, containing acetaldehyde, are withdrawn via conduit 44.

Illustrative conditions for the process of FIG. 1 are given in U.S. Pat. No. 3,904,656.

In the operation of the FIG. 1 process, the ethylene oxide overhead product removed via conduit 42 will generally contain more than 10 ppm of formaldehyde. Since this amount is too high for certain purposes, the formaldehyde content must be lowered by further purification, as for example, by use of the method of U.S. Pat. No. 3,418,338 which has been discussed above.

However, it has been surprisingly discovered that the need to use such additional purification methods is avoided in accordance with the process of the present invention by which a refined ethylene oxide substantially free of aldehydic impurities, containing not greater than about 10 ppm aldehydic impurities can be produced. Thus, the process of FIG. 1 is modified in accordance with this invention as set forth in FIGS. 2 through 7.

Figure 2:
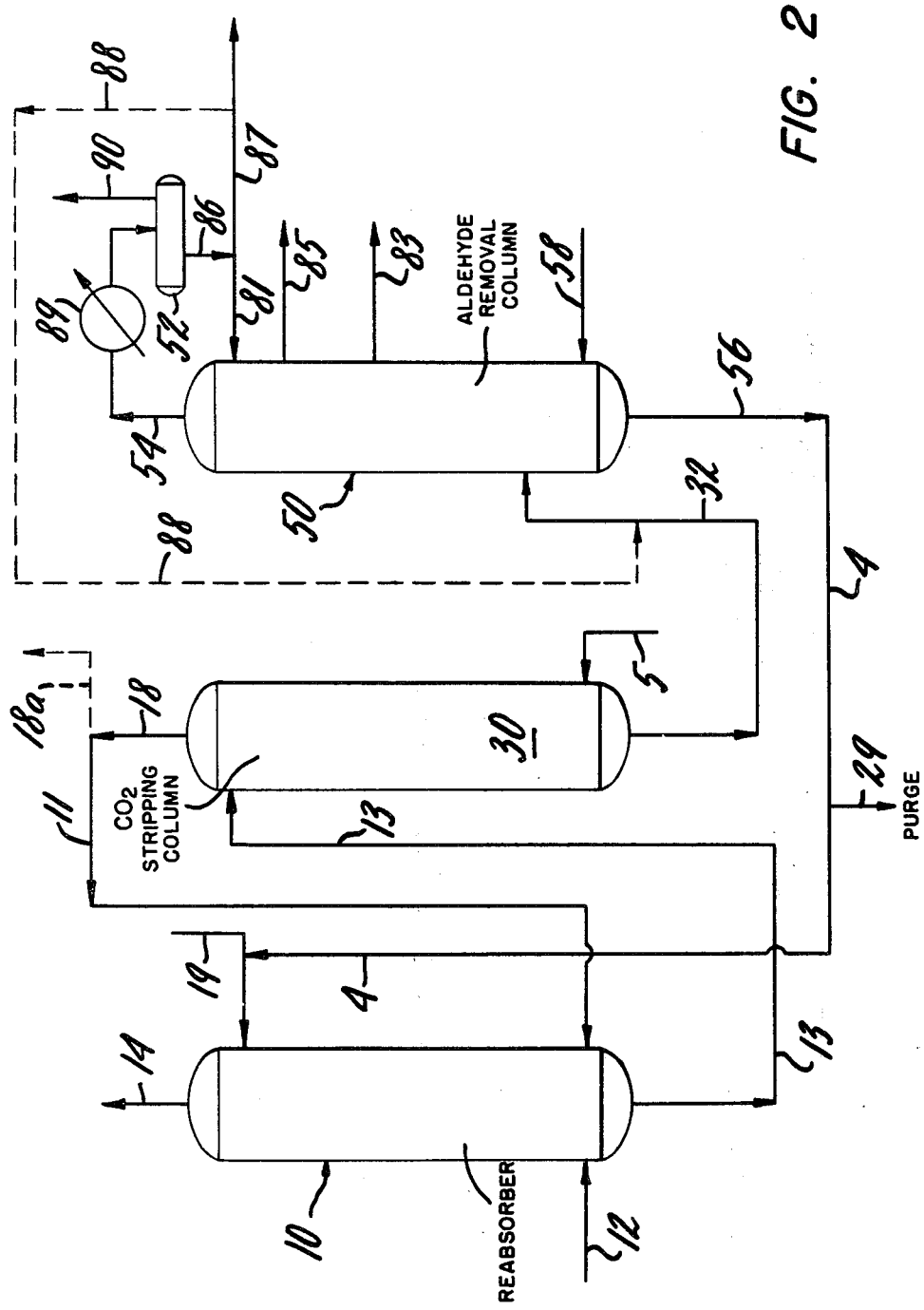
FIG. 2 is a diagrammatic illustration of the overall process of the present invention for recovering ethylene oxide incorporating the improved method.

In one embodiment of the process of the present invention, as shown in FIG. 2, the process of FIG. 1 is modified to employ a novel multi-stage distillation column for separation of aldehydic impurities and to obtain as a side stream an ethylene oxide stream containing the desired low concentrations of aldehydic impurities.

In the process of FIG. 2, the vapor and liquid mixture containing ethylene oxide, $CO_2$, gaseous inerts, water and aldehydic impurities which is obtained from a conventional stripper (not shown) is fed to reabsorber 10 via conduit 12 wherein it is contacted in a countercurrent fashion with an aqueous medium introduced to column 10 via conduit 19 to absorb ethylene oxide, thereby resulting in a reabsorbate which is withdrawn via conduit 13. Unabsorbed gases, including carbon dioxide, are withdrawn from the upper portion of column 10 via conduit 14. Bottoms withdrawn from column 10 via conduit 13 are passed to the upper portion of carbon dioxide stripping column 30 wherein the liquid is contacted, in countercurrent fashion, with stripping fluid such as steam (or other fluid such as $N_2$), to vaporize absorbed gases, including carbon dioxide, which are removed from the upper portion of column 30 and recycled to column 10 via conduit 11 for absorption of any residual ethylene oxide remaining in these gases. Unabsorbed gases such as carbon dioxide passing to column 10 via conduit 11 are withdrawn therefrom via conduit 14. Optionally, as where the ethylene oxide content of the gases passing from the upper portion of column 30 are sufficiently low (e.g., by use of a water wash step — not shown), the gases in conduit 18 can be vented directly. Bottoms withdrawn via conduit 32 from column 30 comprise an impure aqueous ethylene oxide solution which is then introduced as feed to column 50 for separation of water and aldehydic impurities therefrom, as will be more fully described below. As is shown, a portion of the aqueous bottoms withdrawn from column 50 via conduit 56 may be recycled via conduits 4 and 19 to column 10 for absorption of additional ethylene oxide. As in FIG. 1, a purge is taken (via conduit 29) from the recycled bottoms in order to remove water and formaldehyde present in the feed to reabsorber 10 and glycol formed in preceding processing. While not critical to the present invention, the amount of such purge will generally range from about 0.1 to 25 weight percent, usually from 1 to 10 weight percent, of the bottoms product passed to line 4.

The operation of carbon dioxide stripping column 30 in the process depicted in FIG. 2 is entirely conventional, and a detailed description thereof is not necessary to a full understanding of the process of the present invention. Thus, column 30, for example, can comprise any suitably configured distillation column, whether packed bed or provided with distillation trays, and will generally possess from about 1 to 20, and more usually from about 5 to 10, minimum theoretical vapor-liquid contacting stages, and will generally employ a bottoms temperature of from about 20° to 100° C., and more usually from about 50° to 70° C., and an overhead pressure of from about 4 to 30 psia, usually from about 15 to 20 psia.

Figure 3:
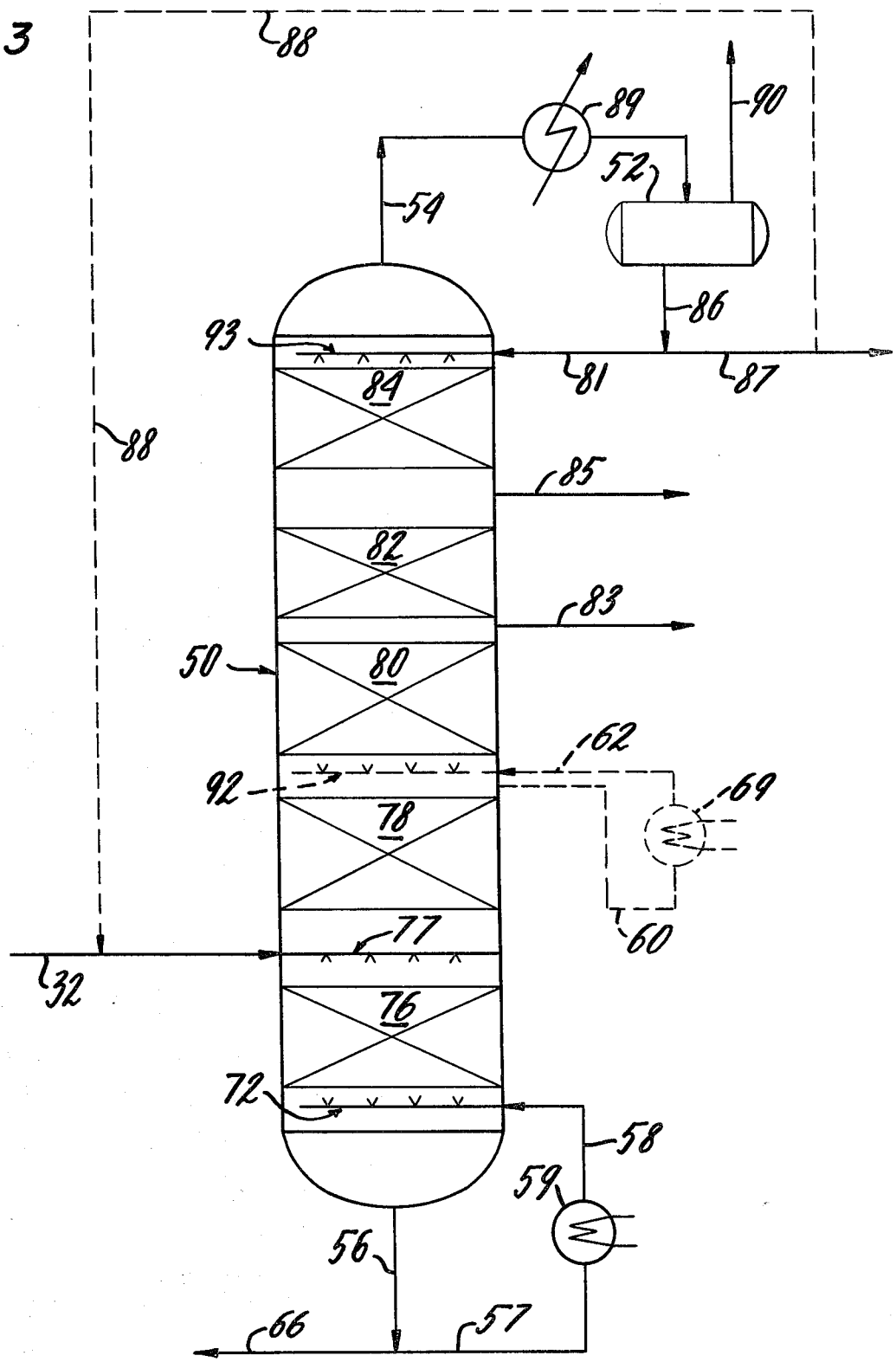
FIG. 3 is a diagrammatic illustration of an embodiment of the process of the present invention which particularizes the aldehyde removal column (50) shown schematically in FIG. 2.

Referring to FIGS. 2 and 3, the impure aqueous ethylene oxide solution, containing aldehydic impurities, is passed via conduit 32 into a multi-stage distillation column, indicated generally at 50, the aldehyde removal column of this invention. The composition of the impure aqueous ethylene oxide solution treated by the present invention for removal of aldehydic impurities therefrom can vary widely. Generally, however, the impure liquid will contain from about 2 to 25 weight percent, usually from about 8 to 12 weight percent, ethylene oxide; from about 75 to 98 weight percent, usually from about 88 to 92 weight percent, water; and from about 0.001 to 0.2 weight percent, usually from about 0.005 to 0.02 weight percent, "aldehydic impurities," as the latter term is defined herein below. The impure liquid will also generally contain up to about 500 ppm by weight, usually up to about 250 ppm by weight, dissolved $CO_2$ (based on the ethylene oxide content of the impure liquid). The molar ratio of water to ethylene oxide in the impure liquid will generally be from about 5:1 to 50:1, preferably from about 10:1 to 30:1, and more preferably from about 15:1 to 25:1.

The term "aldehydic impurities" as used herein is intended to refer to a member of the group consisting of formaldehyde, acetaldehyde and mixtures thereof. In the case of mixtures of aldehydic impurities, the relative amounts of such impurities are not critical to the present invention. Typically, the impure aqueous ethylene oxide solution will contain up to 0.1 weight percent, usually from 0.005 to 0.05 weight percent, formaldehyde, and from about 0.001 to 0.1 weight percent, usually from about 0.002 to 0.05 weight percent, acetaldehyde. However, impure ethylene oxide solutions containing formaldehyde and acetaldehyde outside the range of the foregoing molar ratio can also be treated by the present invention.

The impure aqueous ethylene oxide solution is introduced to aldehyde removal column 50 via distributing member 77, which may comprise any of the conventional liquid distributor heads commonly used with such liquids. Column 50 is provided with the following fractionation regions, which are positioned in ascending order above conduit 32: first fractionation region 78 at least one theoretical vapor-liquid contacting stage, preferably having from 1 to 20, and more preferably from 2 to 10, theoretical vapor-liquid contacting stages; second fractionation region of at least one theoretical vapor-liquid contacting stage, preferably having from 1 to 15, and more preferably from 2 to 6, theoretical vapor-liquid contacting stages; third fractionation region 82 of at least 5 theoretical vapor-liquid contacting stages, preferably having from 10 to 60, and more preferably from 15 to 50, theoretical vapor-liquid contacting stages; and fourth fractionation region 84 of at least one theoretical vapor-liquid contacting stage, preferably having from 1 to 20, and more preferably from 2 to 10, theoretical vapor-liquid contacting stages. Fifth fractionation region 76, having at least one theoretical vapor-liquid contacting stage, and preferably having from 1 to 20, and more preferably from 3 to 12, theoretical vapor-liquid contacting stages, is provided within column 50 below conduit 32. Most preferably, first fractionation region 78 has from 4 to 7 theoretical vapor-liquid contacting stages, second fractionation region 80 has from 2 to 4 theoretical vapor-liquid contacting stages, third fractionation region 82 has from 25 to 40 theoretical vapor-liquid contacting stages, fourth fractionation region 84 has from 2 to 5 theoretical vapor-liquid contacting stages and fifth fractionation region 76 has from 4 to 8 theoretical vapor-liquid contacting stages.

The vapor-liquid contacting stages in column 50 can comprise any of the conventional distillation trays which are adapted for countercurrent vapor-liquid contacting and include sieve trays, bubble cap trays, valve trays, tunnel cap trays and the like. In addition one or more of the various fractionation regions within column 50 can comprise packings which are substantially inert to the components of the vapor and liquid contained in the column. Suitable packing therefore include Berle saddles, Raschig rings, Intalox saddles and the like. Both distillation trays and packed sections can be employed within the same column.

In the operation of column 50, upwardly flowing vapors and downwardly flowing liquids are countercurrently contacted within each fractionation region. The liquid feed, which is preferably introduced to column 50 substantially uniformly across the diameter of the column, is at least partially vaporized therein. The liquid collecting in the lower portion of column 50 is withdrawn as bottoms product via conduit 56 and comprises an aqueous solution containing generally less than about 0.1 weight percent, and preferably less than about 0.01 weight percent, ethylene oxide; generally less than about 0.1 weight percent formaldehyde; generally less than about 0.001 weight percent acetaldehyde; and generally from about 0.5 to 20 weight percent, preferably from about 1 to 5 weight percent, ethylene glycol; and is most preferably substantially free of ethylene oxide, that is, contains less than about 0.001 weight percent ethylene oxide. However, the precise composition can vary widely; for example, aqueous bottoms containing ethylene glycol in higher or lower concentrations can also be obtained.

Stripping vapor, which can comprise steam or other suitable inert heating medium, is introduced via conduit 58 to column 50 below fifth fractionation region 76. Preferably, a portion of the withdrawn bottoms is recycled via conduit 58 and reboiler 59 to column 50 to provide the necessary stripping vapor for operation of the column. The portion of the bottoms which is not so recycled is passed to conduit 66, and after cooling can be suitably passed to a reabsorber (e.g., to column 10 via conduits 4 and 19 in FIG. 2) for absorption of additional quantities of ethylene oxide.

Figure 4:
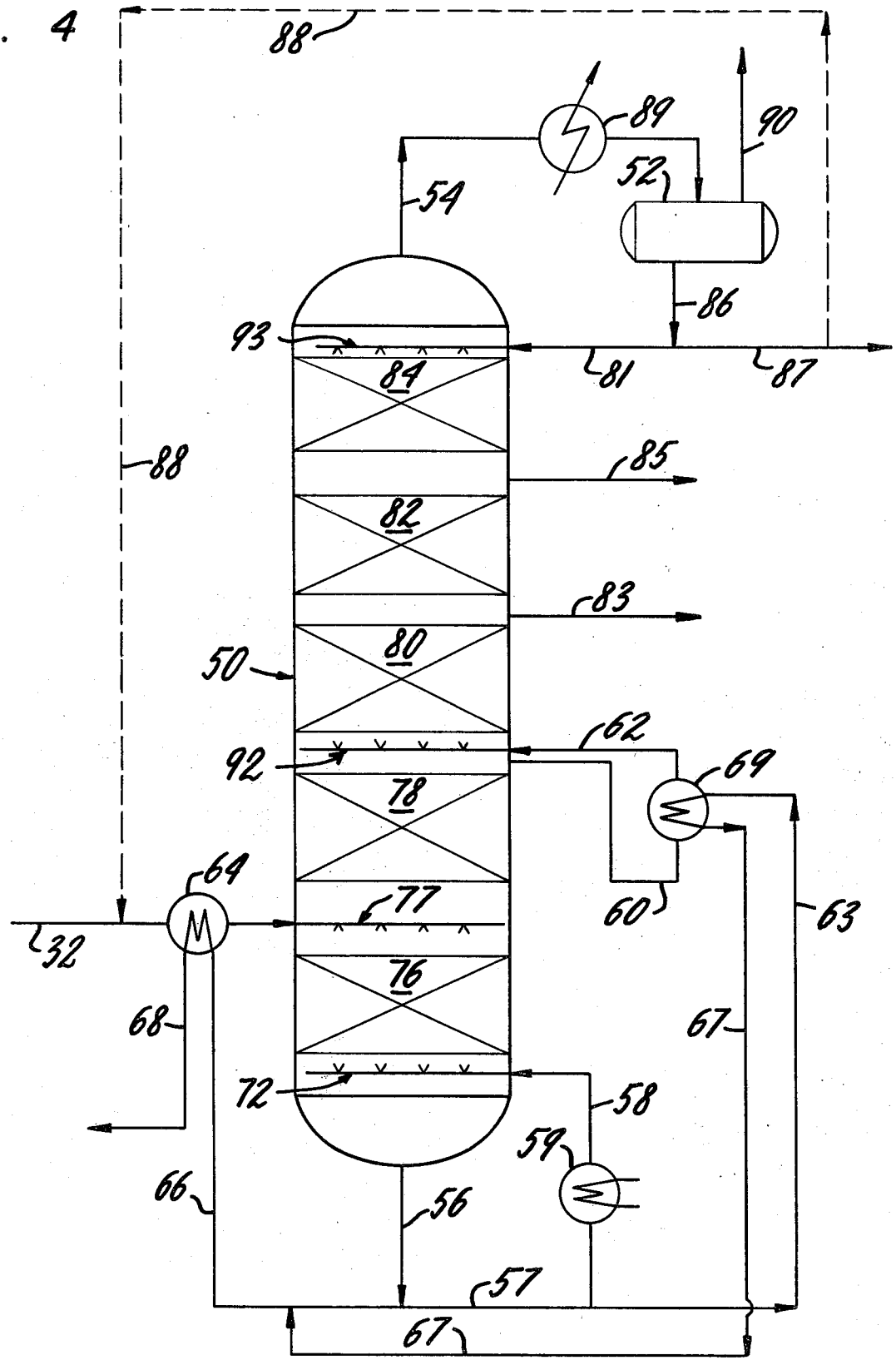
FIG. 4 is a diagrammatic illustration of a second and preferred embodiment of the process of the present invention utilizing reboilers 59 and 69, the latter being heated by means of a portion of the bottoms withdrawn from column 50.

Stripping vapor is also preferably introduced to column 50 between first fractionation region 78 and second fractionation region 80. This side stream stripping vapor is preferably provided by withdrawing at least a portion of the liquid downflowing from second fractionation region 80 and passing the withdrawn liquid via conduit 60 to side stream heat exchanger 69 in which the withdrawn side stream liquid is heated (e.g., by the use of a portion of the bottoms as shown in FIG. 4) to vaporize at least a portion of the withdrawn liquid. The resulting vapor and liquid is then reintroduced to column 50 via conduit 62 and distributing member 92. However, steam or other suitable inert heating medium can also be passed to column 50 via conduit 62 to provide the side stream stripping vapor.

When side stream stripping vapor is used, it is preferred that the amount of heat introduced to column 50 by means of such vapor in conduit 62 be at least about 5%, preferably from about 10 to 70%, and most preferably from about 25 to 50%, of the total stripping heat supplied to column 50. The term "total stripping heat" is herein meant to refer to the sum of the sensible and latent heat introduced to column 50 via conduits 58 and 62. While some heat is also introduced to column 50 via the feed (conduit 32) and liquid reflux (conduit 81), these streams are not to be considered in the determination of the "total stripping heat" in accordance with the above-given definition. The temperature of the heated liquid and vapor introduced to column 50 via conduit 62 is usually from about 40° to 80° C., and preferably from about 50° to 60° C. Likewise, the temperature of fluid introduced to column 50 via conduit 58 is usually from about 130° to 160° C., and preferably from about 140° to 150° C. However, higher or lower temperature can also be used in conduits 58 to 62, and the particular temperature selected will depend on a variety of factors obvious to the skilled practioner, including liquid composition, column pressure and other factors.

A portion of the liquid down-flowing from third fractionation region 82 is withdrawn from column 50 via conduit 83 and comprises an acetaldehyde-rich, ethylene oxide stream. While the composition of this stream will vary widely, depending on such factors as the acetaldehyde content in the impure ethylene oxide feed introduced to column 50 via conduit 32, the temperature and pressure conditions employed in column 50 and other factors, it will generally contain at least about 88 weight percent, and preferably at least about 95 weight percent, ethylene oxide; generally from about 0.05 to 2 weight percent, usually from about 0.3 to 1 weight percent, water; and generally from about 0.1 to 10 weight percent, usually from about 0.2 to 2 weight percent, acetaldehyde, and is generally substantially free of formaldehyde, usually containing less than about 0.005 weight percent of formaldehyde. This acetaldehyde-rich ethylene oxide stream can be treated by conventional techniques to recover additional ethylene oxide, or can be fed to a process in which the acetaldehyde content of the ethylene oxide stream can be tolerated, e.g., in the hydrolysis of ethylene oxide to ethylene glycol by the process disclosed in U.S. Pat. No. 3,904,656.

A portion of the liquid down-flowing from fourth fractionation region 84 is withdrawn from column 50 via conduit 85 and comprises the desired ethylene oxide product containing the desired low concentrations of water and aldehydic impurities. While the precise composition of this ethylene oxide product will also vary depending on such factors as the temperature and pressure conditions in column 50, the number of vapor liquid contacting stages employed, the desired purity of the ethylene oxide product and other factors, the ethylene oxide product stream withdrawn via conduit 85 will be substantially free of aldehydic impurities and water, and will generally contain less than about 20 ppm, usually less than about 5 ppm, formaldehyde; generally less than about 50 ppm, usually less than about 5 ppm, acetaldehyde; and generally less than about 300 ppm, usually less than about 100 ppm, water.

Vapors are withdrawn from the upper portion of column 50 via conduit 54 and passed to condenser 89, which preferably comprises a partial condenser. The effluent from condenser 89 is passed to vapor-liquid separator 52, from which liquid is withdrawn via conduit 86. A portion of this liquid, which comprises an ethylene oxide-rich, formaldehyde containing stream, is recycled via conduit 81 and distributing member 93 to column 50 above fourth fractionation region 84 as liquid reflux. The remaining condensate is withdrawn via conduit 87 and comprises the formaldehyde-rich ethylene oxide stream. While the precise composition of the liquid withdrawn via conduit 87 may vary widely, the liquid will contain generally at least about 99.5 weight percent, ethylene oxide; and generally from about 0.005 to 0.05 weight percent, usually from about 0.1 to 0.3 weight percent, formaldehyde. This liquid will generally be substantially free of acetaldehyde, generally containing less than about 50 ppm acetaldehyde, and will also generally be substantially free of water, usually containing less than about 300 ppm of water. The ethylene oxide content of this formaldehyde-rich stream can vary widely, as is stated above, but will generally comprise up to about 25 weight percent, preferably up to about 15 weight percent, and most preferably up to about 10 weight percent, of the ethylene oxide fed to column 50 via impure ethylene oxide feed introduced through conduit 32.

The quantity of condensate recycled as reflux to column 50 via conduit 81, the quantity of liquid withdrawn as the formaldehyde-rich stream via conduit 87, and the quantity of ethylene oxide product stream withdrawn via conduit 85 can vary widely. However, for most efficient operation, the internal liquid reflux ratio for column 50 be at least about 1.35:1, and preferably from about 1.35:1 to 10:1, more preferably from about 3.5:1 to 7.5:1, and most preferably from about 4.0:1 to 6.0:1, wherein the internal liquid reflux ratio is defined by the following expression (I):

$$R = L/P + F \qquad (I)$$

wherein "R" is the internal liquid reflux ratio, "L" is the moles per hour of liquid downflowing from the fourth fractionation region (i.e., zone 84 in FIG. 2) which is not withdrawn as the ethylene oxide product stream (i.e., not withdrawn via conduit 85 in the embodiment of FIG. 2), "P" is the moles per hour of liquid withdrawn as the ethylene oxide product stream (i.e., via conduit 85 in FIG. 2) and "F" is the moles per hour of liquid withdrawn as the formaldehyde-rich stream (i.e., via conduit 87 in FIG. 2).

The moles per hour of vapor and liquid streams referred to above with respect to expression (I) can be determined employing conventional techniques, and the rates of flow in these various streams to achieve the desired internal liquid reflux ratio can also be controlled by conventional methods, such as by positioning any suitable flow control valves in conduits 81 and 87, and a discussion here of such measurement techniques and flow control methods is not necessary to a full understanding of the present invention.

To the extent that additional quantities of formaldehyde and/or acetaldehyde can be tolerated in the ethylene oxide produced by this process, a portion of either the formaldehyde-rich stream or the acetaldehyde-rich stream, or both, can be admixed with the ethylene oxide product stream to obtain a resultant ethylene oxide-containing liquid having formaldehyde and acetaldehyde content not in excess of that maximum concentrations of these impurities which are desired. Alternatively, the formaldehyde-rich and acetaldehyde-rich streams withdrawn via conduits 87 and 83, respectively, can be further treated for removal of the formaldehyde and/or acetaldehdye content thereof (e.g., by extractive distillation employing the method of U.S. Pat. No. 3,418,338 for formaldehyde removal and distillation for acetaldehyde removal), or can be used directly as feed to a process in which the formaldehyde and acetaldehyde impurities may be tolerated, as for example in the production of ethylene glycol by hydrolysis of the ethylene oxide content of these purged streams. Preferably, however, at least a portion of the formaldehyde-rich ethylene oxide stream in conduit 87 is passed via conduit 88 to conduit 32 and thereby recycled to aldehyde removal column 50 so as to absorb additional quantities of formaldehyde in zone 76 for removal via conduit 56, and to maximize the quantity of ethylene oxide product withdrawn via conduit 85. If desired, up to 100% of the formaldehyde-rich stream in conduit 87 can be recycled via conduit 88.

Vapors formed in separator 52 can be withdrawn therefrom via conduit 90, and are preferably recycled to the feed conduit 12 of reabsorber 10, to avoid buildup in column 50 of carbon dioxide and other gaseous inerts introduced to column 50 via conduit 32.

Alternatively, or in addition, a portion or all of the formaldehyde-rich ethylene oxide stream in conduit 88 can be combined with the vapors in conduit 90 for recycle of such mixed stream to the reabsorber.

While the quantity of liquid in conduit 87 and vapors in conduit 90 can vary widely, generally, the total of the amount of liquid passed to conduit 87 via conduit 86 and vapors i conduit 90 will comprise from about 5 to 20 percent, and more preferably from about 5 to 10 percent, of the feed to column 50 via conduit 32, based on the ethylene oxide content of the feed. Generally, vapors in conduit 90 will comprise from about 25 to 50 percent of the total amount of liquid and vapor passed to conduits 87 and 90.

The quantity of the ethylene oxide-rich, formaldehyde stream recycled to either column 50 or reabsorber 10 is not critical to the present invention, and will be determined by economics of recovery of additional quantities of ethylene oxide from the recycled stream.

The pressures employed in column 50 can vary widely and will of course depend on a variety of factors, such as the composition of the impure liquid feed, the temperatures selected for use in the column, the degree of removal of aldehydic impurities desired, and other factors, but will generally be from about 25 to 100 psig, usually from about 35 to 50 psig. However, higher or lower pressures can also be used.

In FIG. 4 there is illustrated a preferred embodiment of the process of the present invention in which a sidestream reboiler 69 is heated by means of a portion of the bottoms withdrawn from column 50 via conduit 56 and passed to reboiler 69 via conduits 57 and 63. Cooled liquid withdrawn from reboiler 69 is passed via conduit 67 to conduit 66. Bottoms product in conduit 66 is passed to heat exchanger 64 to preheat the liquid feed contained in conduit 32, and the cooled bottoms, which can be withdrawn from heat exchanger 64 via conduit 68, can then after further cooling be suitably recycled to a reabsorber, as described above with respect to FIG. 3, for absorption of additional quantities of ethylene oxide. The relative amounts of withdrawn bottoms in conduit 56 which are passed to reboiler 59 or to heat exchanger 64, both directly via conduit 66 or indirectly via sidestream reboiler 69, can be easily ascertained by the skilled practitioner and will vary widely depending on such factors as bottoms composition, the amount of heat to be imparted to column 50 via conduits 58 and 62, and the like.

Of course, if the necessary temperature in sidestream reboiler 69 cannot be attained by recycle of withdrawn bottoms as discussed above, reboiler 69 can be augmented by a second heat exchanger (not shown) to provide the necessary heating capacity for vaporization of the desired portion of fluid in conduit 60, or reboiler 69 can be provided with an additional source of heating fluid such as steam by suitable means (not shown).

Figure 5:
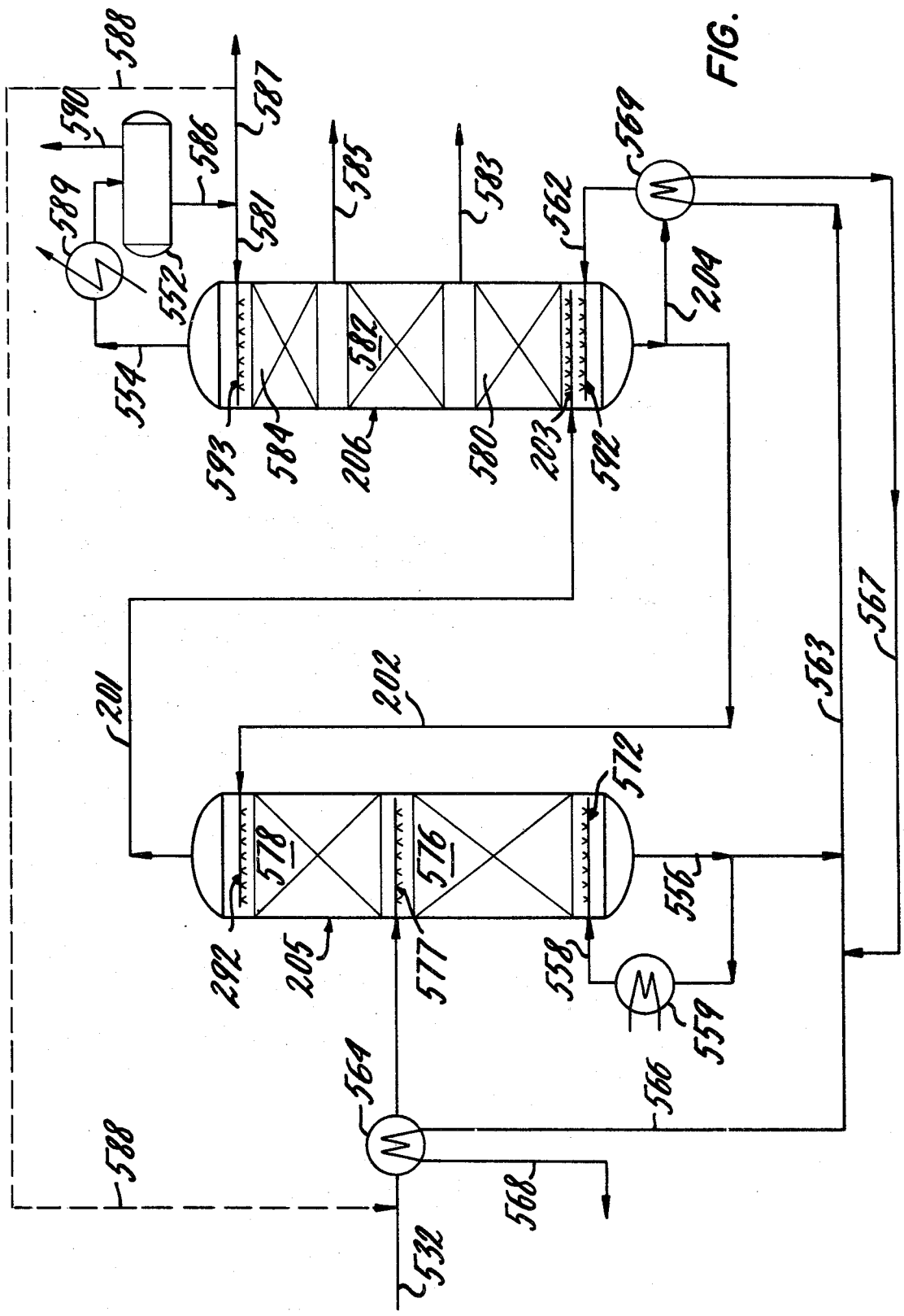
FIG. 5 is a diagrammatic illustration of a third embodiment of the process of the present invention in which the column (50) of FIG. 4 is divided into two separate columns (205 and 206).

Referring now to FIG. 5, wherein identifying numerals are preceded by the number "5" for structure corresponding to that of the embodiment of FIG. 4, there is illustrated an embodiment of the process of this invention in which the multi-stage countercurrent distillation performed in column 50 of of FIG. 4 is effected in two separate distillation columns, i.e., aldehyde removal columns 205 and 206. In this embodiment, the impure ethylene oxide liquid to be treated is introduced via conduit 532 into first distillation column 205, employing distributing member 577. With column 205 there is provided an upper distillation zone 578 and lower distillation zone 576. Overheads product are withdrawn from column 205 via conduit 201 and introduced as feed to the lower portion of column 206 via distributing member 203. A first portion of the bottoms product withdrawn from column 205 via conduit 556 is recycled preferably via conduit 566, heat exchanger 564 and conduit 568 to a reabsorber (e.g., reabsorber 10 in the process of FIG. 2), as described previously. A second portion of the withdrawn bottoms product is recycled to column 205 via reboiler 559, conduit 558 and distributing member 572 to the lower portion of column 205 below zone 576.

Column 206 is provided, in ascending order above the feed thereto, with distillation zones 580, 582 and 584. Overhead product is withdrawn from column 206 via conduit 554, condensed in condenser 589, and the effluent so produced being passed to vapor-liquid separator 552. From separator 552 liquid is withdrawn via conduit 586 and a portion of the withdrawn liquid is recycled via conduits 586 and 581 as liquid reflux to the upper portion of column 206. The remaining portion of this liquid is withdrawn via conduit 587 and comprises the formaldehyde-rich, ethylene oxide stream. The ethylene oxide product stream, substantially free of aldehydic impurities, is withdrawn as a sidestream via conduit 585 from a portion of the liquid downflowing from zone 584, as described previously for the operation of column 50 in FIGS. 2 to 4. Likewise, the acetaldehyde-rich, ethylene oxide stream is withdrawn via conduit 583 and comprises a portion of the liquid downflowing from zone 582.

As described previously, a portion of the formaldehyde-rich, ethylene oxide stream in conduit 587 can be recycled via conduits 588 and 532 to column 205, and vapors withdrawn from separator 552 via conduit 590 can be recycled to a reabsorber (not shown).

Liquid bottoms are withdrawn from column 206 via conduit 202 and in part recycled via distributing member 292 to the upper portion of column 205 and caused to flow downwardly into zone 578. A second portion of the liquid bottoms withdrawn from column 206 is recycled thereto via conduit 204, reboiler 569, conduit 562 and distributing member 592. The bottoms so recycled via line 562 preferably introduces to column 206 at least about 5 percent, more preferably from about 10 to 70 percent, and most preferably from about 25 to 50 percent, of the "total stripping heat" supplied to column 205 and 206, i.e., the sum of the sensible and latent heat introduced via conduits 558 and 562. Preferably, a portion of the liquid bottoms withdrawn from column 205 is passed via conduit 563 to reboiler 569 so as to provide the heat necessary to operate column 206, the cooled liquid being withdrawn from reboiler 569 via 567 and recycled to conduit 566 as shown.

As will be apparent from the foregoing, distillation zone 578 comprises the first fractionation region of at least one theoretical vapor-liquid contacting stage, and preferably of from 1 to 20 and more preferably from 2 to 10, theoretical vapor-liquid contacting stages, and distillation zone 580 comprises the second fractionation region of at least one theoretical vapor-liquid contacting stage, and preferably of from 1 to 15, and more preferably from 2 to 6, theoretical vapor-contacting stages. Likewise, distillation zone 582 comprises the third fractionation region of at least 5 theoretical vapor-liquid contacting stages, and preferably of from 10 to 60, and more preferably 15 to 50, theoretical vapor-liquid contacting stages, and distillation zone 584 comprises the fourth fractionation region of at least one theoretical-liquid contacting stage, and preferably of from 1 to 20, and more preferably from 2 to 10, theoretical vapor-liquid contacting stages. Finally, distillation zone 576 comprises the fifth fractionation region of at least one theoretical vapor-liquid contacting stage and preferably of from 1 to 20, and more preferably from 3 to 12, theoretical vapor-liquid contacting stages.

As in the embodiments of FIGS. 2 to 4, most efficient operation of the embodiment of FIG. 5 requires use of an internal reflux ratio for column 206 of at least about 1.35:1, and preferably from 1.35:1 to 10:1, more preferably from about 3.5:1 to 7.5:1, and most preferably from about 4.0:1 to 6.0:1, wherein the internal liquid reflux ratio is defined by expression (I) above as applied to the similarly denoted zones and streams in the embodiment of FIG. 5.

Figure 6:
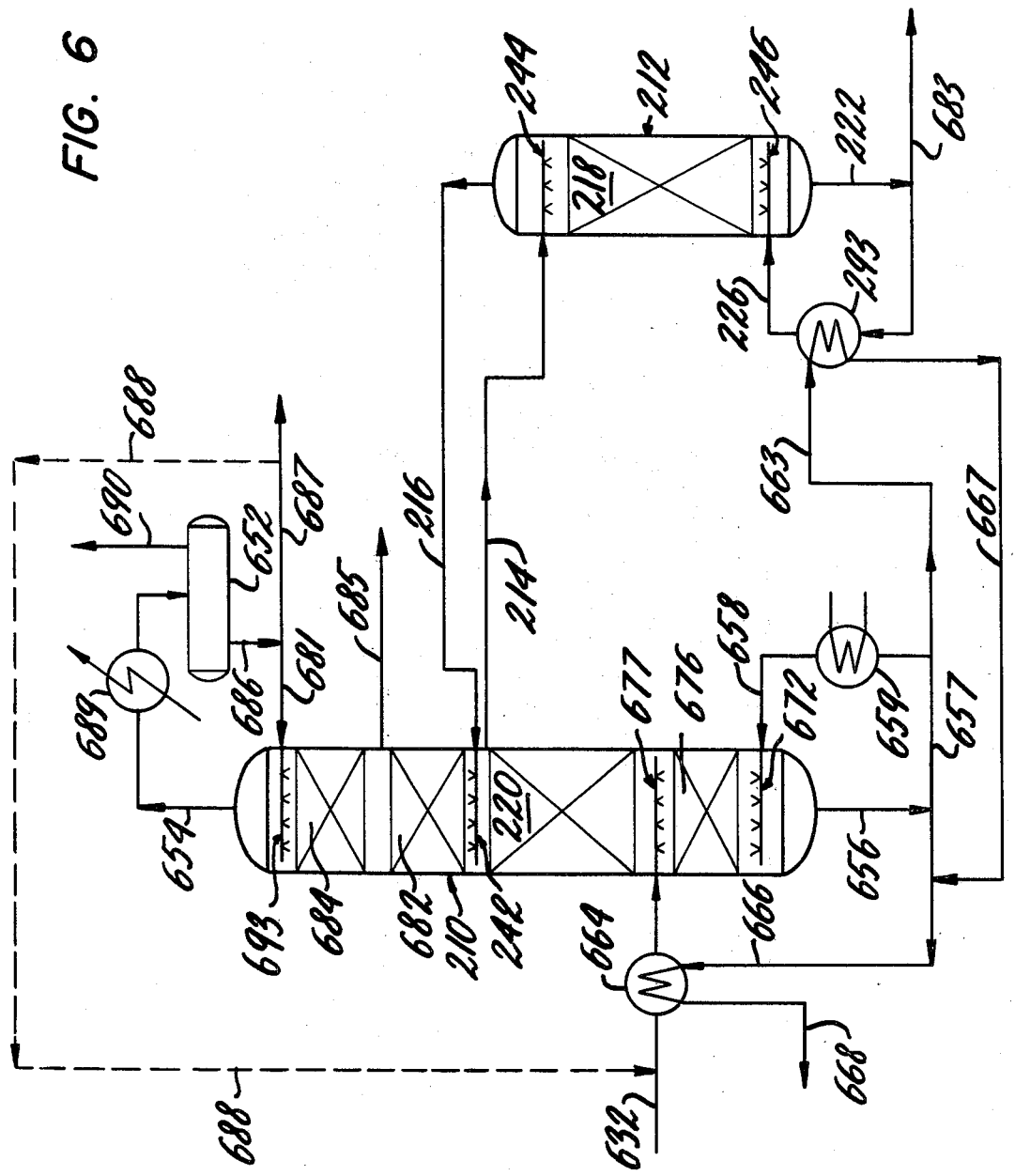
FIG. 6 is a diagrammatic illustration of a fourth embodiment of the process of the present invention in which a side stream stripping column (212) is employed in combination with the aldehyde removal column (210) to further remove acetaldehyde.

Yet another embodiment of the process of this invention is shown in FIG. 6, in which numerals employing the prefix number "6" refers to the same or similar elements in FIGS. 2 to 4. In this embodiment a sidestream stripping column 212, as discussed more fully below, is employed to further concentrate the acetaldehyde content of the acetaldehyde-rich ethylene oxide stream. In FIG. 6, an impure ethylene oxide stream containing aldehydic impurities is introduced via conduit 632 into distillation column 210, employing distributing member 677. Within aldehyde removal column 210 the following distillation zones are disposed in ascending order above the feed: the first distillation zone 220, second distillation zone 682 and third distillation zone 684. As will be described more fully below, these three distillation zones, in combination with sidestream stripper 212, perform the functions of distillation zones 76, 80, 82 and 84 in the apparatus of FIGS. 2 to 4.

In this embodiment, therefore, distillation zone 220 corresponds to first and second fractionation regions 76 and 80 and therefore possesses at least two theoretical vapor-liquid contacting stages, and preferably from 2 to 35, more preferably from 4 to 16, and most preferably from about 6 to 11, theoretical vapor-liquid contacting stages. Distillation zones 682 and 684, which correspond to distillation zones 82 and 84, respectively, in the apparatus of FIGS. 3 to 4 and which therefore comprise the third and fourth fractionation regions, respectively, employ the number of theoretical vapor-liquid contacting stages discussed above for zones 82 and 84.

Overhead product produced in column 210 is withdrawn therefrom via conduit 654 and passed to partial condenser 689, from which effluent is passed to vapor-liquid separator 652. Liquid separated therein is withdrawn via conduit 686 and is in part recycled as liquid reflux to column 210 via conduit 681 and distributing member 693, with the remainder being withdrawn via conduit 687 as the formaldehyde-rich stream. The ethylene oxide product stream substantially free of aldehydic impurities is withdrawn from the column via conduit 685, and comprises a portion of the liquid downflowing from distillation zone 684, as described previously.

A portion of the liquid down-flowing from zone 682 is withdrawn via conduit 214. This liquid, which comprises the combined sidestream withdrawn, e.g., in the embodiment of FIGS. 2–4 via conduits 60 and 83, is passed to the upper portion of sidestream distillation column 121 in which is provided a distillation zone 218 which comprises a sixth fractionation region of at least one theoretical vapor-liquid contacting stage, and preferably having from 2 to 50, more preferably from 5 to 30, and most preferably from 10 to 20, theoretical vapor-liquid contacting stages. The vapor produced in column 212 is withdrawn therefrom via conduit 216 and reintroduced to column 210 below zone 682 via distributing member 242. Liquid bottoms produced in column 212 are withdrawn therefrom via conduit 222 of which a portion is passed to conduit 683 and withdrawn from the system as the acetaldehyde-rich stream. A portion of the withdrawn bottoms can be recycled to column 212 via conduit 226 and reboiler 293, which can be suitably heated with a portion of the bottoms product from column 210, which can be passed to reboiler 293, for example, via conduits 657 and 663. The cooled heating fluid can be recycled via conduit 667 to conduit 666, as described previously.

In the embodiment of FIG. 6, distillation zone 676 below the feed to column 210 comprises the fifth fractionation region, and its operation has been described previously. As before, a portion of the bottoms withdrawn from column 210 can be recycled thereto via a suitable heat exchanger 659, with the remaining bottoms being preferably passed either directly to heat exchanger 224 as described previously or passed via conduit 666 to heat exchanger 664 and then recycled to a suitable reabsorber 10 via conduit 668.

The internal liquid reflux ratio for most efficient operation of the embodiment of FIG. 6 is at least about 1.35:1, and preferably from about 1.35:1 to 10:1, more preferably from about 3.5:1 to 7.5:1 and most preferably from about 4.0:1 to 6.0:1, wherein this internal liquid reflux ratio is defined by expression (I) above having reference to the corresponding zones and streams in the embodiment of FIG. 6.

Likewise, the liquid and vapor recycled column 212 via conduit 226 preferably introduces at least about 5 percent, preferably from about 10 to 70 percent, and most preferably from about 25 to 50 percent, of the "total stripping heat" supplied to columns 210 and 212, i.e., the sum of the sensible and latent heat introduced via conduits 658 and 216.

If desired, a portion of the formaldehyde-rich ethylene oxide stream in conduit 687 may be recycled via conduits 688 and 632 to column 210, and a portion of vapors withdrawn from separator 652 via conduit 690 may be recycled to a reabsorber (not shown), as described previously.

As indicated above, the process illustrated in FIG. 6 is particularly useful when, for example, it is desired to minimize the amount of liquid withdrawn via conduit 683 as the acetaldehyde-rich ethylene oxide stream.

When thus practiced, at steady-state conditions, the flow rate of the acetaldehyde-rich ethylene oxide stream in conduit 683 is generally from about 0.1 to 10 percent of the flow rate of the ethylene oxide product stream which is withdrawn via conduit 685. This should be compared to the flow rate of the acetaldehyde-rich ethylene oxide streams in conduits 83 (FIGS. 3 and 4) and 538 (FIG. 5) which is generally from about 0.5 to 15 percent of the flow rate of the ethylene oxide product streams in conduits 85 and 585, respectively. Of course, in any of the foregoing embodiments, the relative flow rates of the acetaldehyde-rich, formaldehyde-rich and product ethylene oxide streams will vary widely depending on the degree of removal of aldehydic impurities desired and can be easily determined by the skilled practitioner. Thus, relative flow rates of the acetaldehyde-rich ethylene oxide stream and the ethylene oxide product stream outside the ranges mentioned above can be employed.

Figure 7:
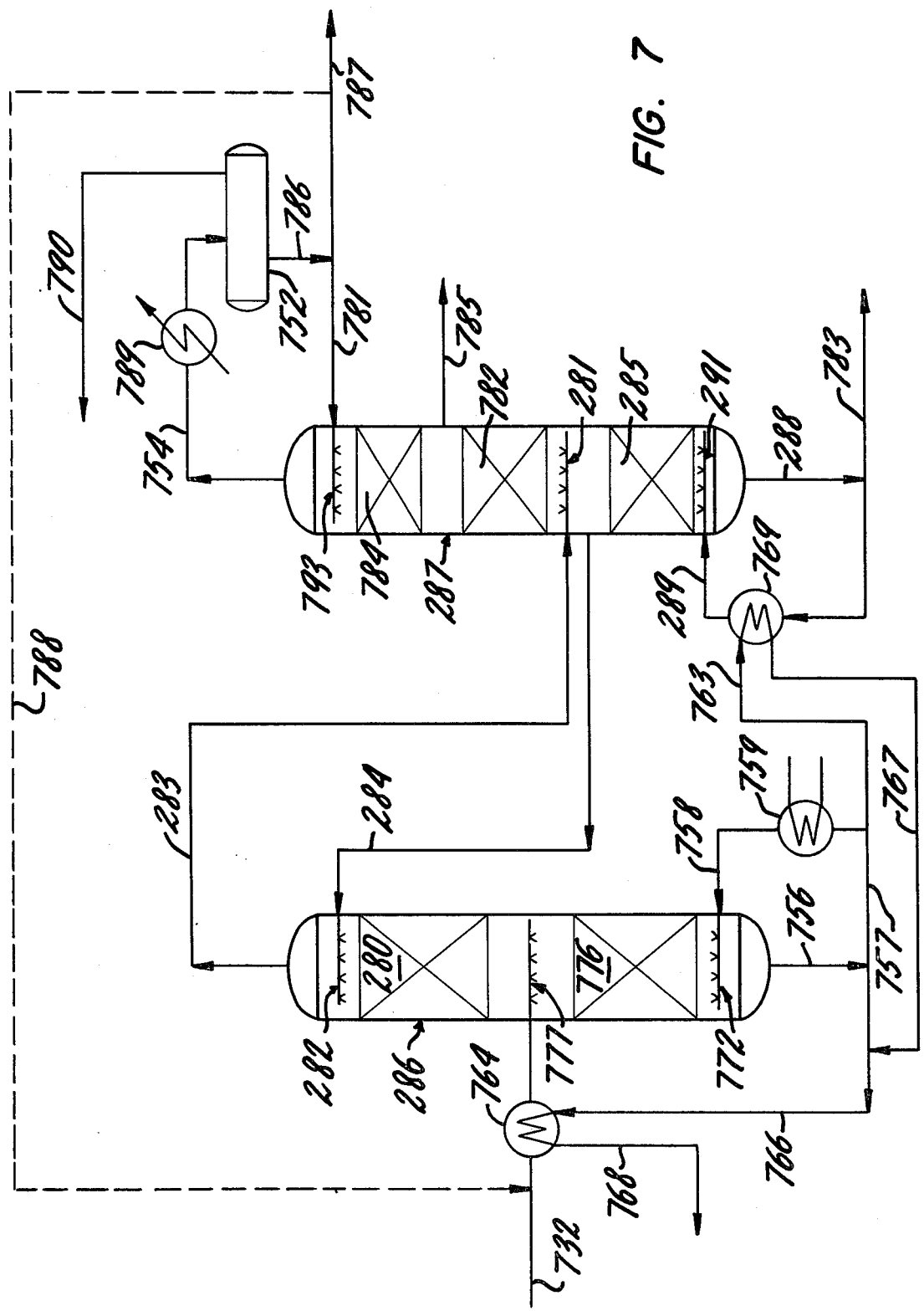
FIG. 7 is a diagrammatic illustration of a fifth embodiment of the process of the present invention in which the second distillation column of FIG. 5 is modified to incorporate an acetaldehyde-concentrating region (285) below the feed to the column.

Reference is now made to FIG. 7, wherein identifying numerals are preceded by the number "7" for structure corresponding to that of the embodiment of FIGS. 2 to 4. In FIG. 7 there is illustrated an embodiment of this invention in which the multi-stage countercurrent distillation performed in column 50 of FIGS. 2 to 4 is effected in two separate distillation columns, i.e., aldehyde-removal columns 286 and 287, column 287 being provide with a distillation zone 285 which performs the same function of distillation zone 218 of FIG. 6, that is, effects a concentration of the acetaldehyde content of the acetaldehyde-rich ethylene oxide stream which is withdrawn via conduit 783 from the process. In this embodiment, the impure ethylene oxide liquid to be treated is introduced via conduit 732 into first distillation column 286, employing distributing member 777. Within column 286 there is provided an upper distillation zone 280 and lower distillation zone 776. Overheads product are withdrawn from column 286 via conduit 283 and introduced as feed to second distillation column 287 via distributing member 281. A first portion of the bottoms product withdrawn from column 286 via conduit 756 is recycled preferably via conduit 766, heat exchanger 764 and conduit 768 to a reabsorber (e.g., reabsorber 10 in the process of FIG. 2), as described previously. A second portion of the withdrawn bottoms product is recycled to column 286 via reboiler 759, conduit 758 and distributing member 772 to the lower portion of the column below zone 776.

Column 287 is provided, in ascending order above the feed thereto, with distillation zones 782 and 784, and is provided with distillation zone 285 below the feed. Overheads product is withdrawn from column 287 via conduit 754, condensed in condenser 789 and the effluent therefrom is passed to vapor-liquid separator 752. Liquid separated in separator 752 is withdrawn via conduit 786 and a portion of the withdrawn liquid is recycled via conduits 781 and distributing member 793 to the upper portion of column 287. The remaining portion of the withdrawn liquid is passed to conduit 787 and comprises the formaldehyde-rich, ethylene oxide stream, of which at least a portion is preferably recycled via conduits 788 and 732 to distillation column 286, as described previously. Vapors withdrawn from separator 752 are preferably recycled via conduit 790 to a reabsorber (not shown), also as described previously.

The ethylene oxide product stream, substantially free of aldehydic impurities, is withdrawn as a sidestream via conduit 785 from a portion of the liquid downflowing from distillation zone 784 as described previously with the operation of column 50 in FIGS. 2 to 4.

A portion of the liquid downflowing from distillation zone 782 is withdrawn via conduit 284 and is passed via distributing member 282 as liquid reflux to column 286. Liquid bottoms produced in column 287 are withdrawn therefrom via conduit 288 and a portion thereof is passed to conduit 783 and withdrawn from the system as the acetaldehyde-rich, ethylene oxide stream. A portion of the withdrawn bottoms is recycled to column 287 via reboilers 769 and conduit 289, which reboiler can be suitably heated with a portion of the bottoms product withdrawn from column 286, and passed to reboiler 769, for example, via conduit 757 and 763. The cooled heating fluid can be recycled via conduit 767 to conduit 766, as described previously.

In the embodiment of FIG. 7, distillation zone 280 corresponds to distillation zone 220 of the embodiment of FIG. 6 and therefore also corresponds to first and second fractionation region 76 and 80 in the embodiments of FIGS. 3 and 4. Distillation zone 280 therefore possesses at least 2 theoretical vapor-liquid contacting stages, and preferably from 2 to 35, more preferably from 4 to 16, and most preferably from 6 to 11, theoretical vapor-liquid contacting stages. Distillation zones 782 and 784, which correspond to distillation zones 82 and 84, respectively, in the apparatus of FIGS. 3 to 4 and which therefore comprise the third and fourth fractionation regions, respectively, employ the number of theoretical vapor-liquid contacting stages discussed above for zones 82 and 84.

Distillation zone 776 below the feed to column 286 comprises the fifth fractionation region, and its operation has been described previously. Distillation zone 285 provided within column 287 below the feed comprises a sixth fractionation region and therefore corrresponds to distillation zone 218 in the embodiment of FIG. 6. Distillation zone 285 therefore possesses at least 1 theoretical vapor-liquid contacting stage, and preferably has from 2 to 50, more preferably from 5 to 30, and most preferably from 10 to 20, theoretical vapor-liquid contacting stages.

As described above for the embodiments of FIGS. 2 through 6, the process of FIG. 7 preferably employs an internal liquid reflux ratio, for most efficient operation of this embodiment, of at least about 1.35:1, and preferably from about 1.35:1 to 10:1, more preferably from about 3.5:1 to 7.5:1, and most preferably from about 4:1 to 6:1, wherein this internal reflux ratio is defined by expression (I) above, having reference to the corresponding zones and streams in the embodiment of FIG. 7.

Likewise, there is preferably introduced into column 287 via conduit 289 at least about 5 percent, preferably from about 10 to 70 percent, and most preferably, from about 25 to 50 percent, of the "total stripping heat" supplied to columns 286 and 287, i.e., the sum of the sensible and latent heat introduced via conduits 758 and 289.

In like manner to the process of FIG. 6, the embodiment of FIG. 7 is particularly useful when it is desired to minimize the amount of liquid withdrawn via conduit 783 as the acetaldehyde-rich ethylene stream. When thus practiced, in steady state conditions, the flow rate of the acetaldehyde-rich ethylene oxide stream in conduit 783 is generally from about 0.1 to 10 percent of the flow rate of the ethylene oxide product stream which is withdrawn via conduit 785. As discussed above in the embodiment of FIG. 7, relative flow rates of the acetaldehyde-rich ethylene oxide stream and the ethylene oxide product stream outside the ranges mentioned above can be employed.

Figure 8:
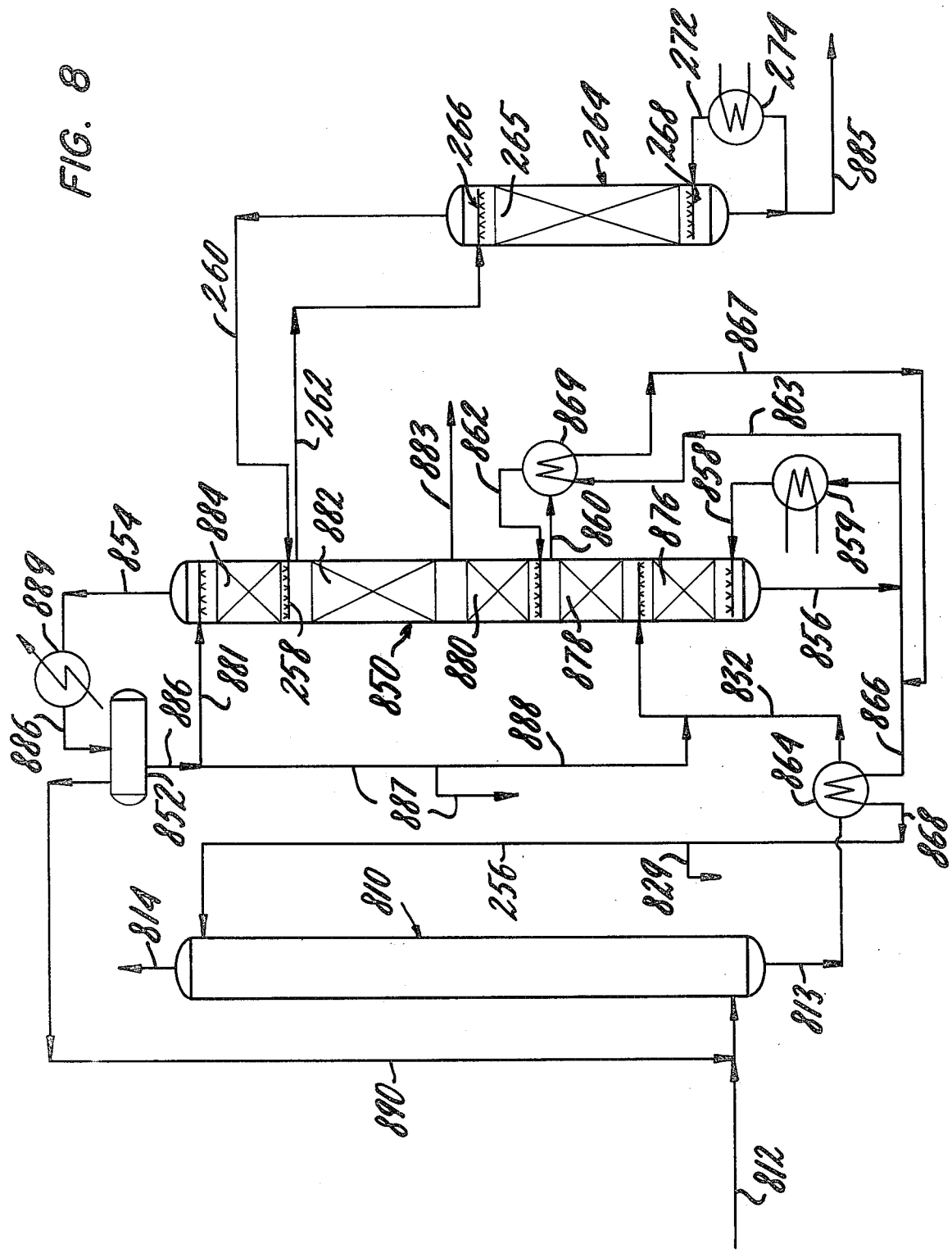
FIG. 8 is a diagrammatic illustration of a sixth embodiment of the overall process of the present invention in which the process of FIG. 2 is modified to allow direct feed of reabsorbate to the aldehyde removal column (850), which is provided with a side stream stripping column (264) for removal of carbon dioxide.

In the embodiment of FIGS. 2 through 7, inclusive, effluent from reabsorber 10 is first treated in carbon dioxide stripping column 30 and the bottoms product from this column is then passed as feed to the aldehyde-removal column(s), as described previously. FIG. 8 illustrates yet another embodiment of this invention in which reabsorbate, containing carbon dioxide gas, is withdrawn from a reabsorbing column 810 and passed directly to an aldehyde removal column 850 which is then provided with a sidestream stripper 264 for removal of carbon dioxide, which removed gases are then reintroduced to the aldehyde removal column and subsequently to the reabsorber for removal with the overhead vapors from the latter column. In FIG. 8, like elements of structure to the embodiments of FIGS. 2 to 4 employ the numerals of those figures preceded by the "8". Thus, in FIG. 8 there is illustrated a process in which an aqueous ethylene oxide solution containing dissolved carbon dioxide and aldehydic impurities, which is obtained from a conventional stripper (not shown), is passed as feed to the lower portion of reabsorber 810 via conduit 812 wherein it is contacted in countercurrent fashion with an aqueous medium introduced to the upper portion of column 810 via conduit 256 to absorb ethylene oxide, thereby resulting in a reabsorbate which is withdrawn via conduit 813. Unabsorbed gases, including carbon dioxide, are withdrawn from the upper portion of column 810 via conduit 814. The bottoms withdrawn from column 810 are passed via conduits 813 and 832 as feed to aldehyde removal column 850, in which is provided, in ascending order above the feed, distillation zones 878, 880, 882 and 884, and in which column there is provided distillation zone 876 below the feed.

The impure aqueous ethylene oxide solution containing aldehydic impurities and dissolved carbon dioxide, which is introduced to aldehyde removal column 850 via conduit 832, can possess a composition which, as for the embodiments of FIGS. 2 through 7, can vary widely. Generally, however, the impure liquid will contain from about 5 to 25 weight percent, usually from about 8 to 15 weight percent, ethylene oxide; from about 75 to 95 weight percent, usually from about 85 to 92 weight percent, water; and from about 0.001 to 0.1 weight percent, usually from about 0.005 to 0.02 weight percent, aldehydic impurities; and will also contain (based on the ethylene oxide content of the impure liquid) greater than about 500 ppm, usually greater than about 1,000 ppm, dissolved carbon dioxide and gaseous inerts.

Distillation zone 878 comprises the first fractionation region and possesses at least one theoretical vapor-liquid contacting stage, and preferably from 1 to 20, more preferably from 2 to 10 theoretical vapor-liquid contacting stages, and distillation zone 880 comprises the second fractionation region and possesses at least one theoretical vapor-liquid contacting stage, preferably from 1 to 12, and more preferably from 2 to 6, theoretical vapor-liquid contacting stages. Likewise, distillation zone 882 comprises the third fractionation region and possesses at least 5 theoretical vapor-liquid contacting stages, and preferably from 10 to 60, and more preferably from 15 to 50, theoretical vapor-liquid contacting stages, and distillation zone 884 comprises the fourth fractionation region and possesses at least 1, preferably from 1 to 20, and more preferably from 2 to 10, theoretical vapor-liquid contacting stages. Finally, distillation zone 876 comprises the fifth fractionation region and possesses at least 1, preferably from 1 to 20, and more preferably from 3 to 12, theoretical vapor-liquid contacting stages.

As in the embodiment of FIGS. 3 and 4, column 850 is preferably provided with conduit 860 to provide means for withdrawing at least a portion of the liquid downflowing distillation zone 880, which withdrawn liquid is heated in heat exchanger 869, as described previously, and recycled via conduit 862 to column 850 below distillation zone 880. Bottoms product are withdrawn from column 880 via conduit 856 and in part recycled to the column (via reboiler 859 and conduit 858) below distillation zone 876. A portion of the withdrawn bottoms is preferably passed to conduit 863 to provide the heating fluid necessary for operation of heat exchanger 869, and the cooled liquid is then withdrawn from the heat exchanger via conduit 867 and passed to conduit 866 and 256 for recycle to reabsorber 810. A portion of the liquid so recycled via conduit 256 can be withdrawn via conduit 829 as purge to avoid build-up in the system of undesired quantities of ethylene glycol and formaldehyde, as described above.

As in the embodiment in FIGS. 2 to 4, an acetaldehyde-rich stream is withdrawn from column 850 via conduit 883 and comprises at least a portion of the liquid downflowing from distillation zone 882. This acetaldehyde-rich stream will generally be withdrawn via conduit 883 at a flow rate equivalent to from about 0.5 to 25 percent of the flow rate of the ethylene oxide product stream in conduit 885, although higher or lower flow rates can also be used.

Since the liquid introduced via conduit 832 to column 850 in the embodiment of FIG. 8 will contain large amounts (e.g., up to about 0.1 weight percent) of dissolved carbon dioxide, there is provided in this embodiment a conduit 262 by which at least a portion of the liquid downflowing from distillation zone 884 is withdrawn from column 850 and introduced to the upper portion of sidestream stripper 264 via distributing member 266. In stripper 264 there is provided distillation zone 265 in which the downflowing liquid so introduced is countercurrently contacted with upwardly flowing vapors which are introduced to stripper 264 by means of distributing member 268 and which result from the treatment in reboiler 274 of a portion of the stripper bottoms which are, in turn, withdrawn from stripper 264 via conduit 272. The remaining portion of bottoms withdrawn from stripper 264 is passed to conduit 885 and comprises the desired ethylene oxide-containing stream which is substantially free of aldehydic impurities and which is also substantially free of $CO_2$, i.e., contains less than about 20 ppm by weight dissolved $CO_2$.

Overhead products formed in stripper 264 are rich in carbon dioxide which has been stripped by treatment of the sidedraw in stripper 264 and are passed from stripper 264 as recycle to column 850 via conduit 260 and distributing member 258, such recycle being introduced to column 860 at a point in the column below distillation zone 884. The combined overhead formed in column 850 is withdrawn therefrom via conduit 854 and passed to condenser 889, which in FIG. 8 is illustrated as a partial condenser. Condensate so produced is passed to gas-liquid separator 852. A portion of the liquid withdrawn from separator 852 is passed via conduits 886 and 881 to the upper portion of column 850 as liquid reflux, the amount of such reflux being sufficient to provide an internal liquid reflux ratio of at least about 1.35:1, and preferably from about 1.35:1 to 10:1, more preferably from about 3.5:1 to 7.5:1, and most preferably from about 4.0:1 to 6.0:1, the internal liquid reflux ratio being defined by expression (I) above, having reference to the zones and streams defined for FIG. 8. The remaining condensate not so refluxed comprises the formaldehyde-rich stream which is withdrawn via conduit 887. At least a portion of this stream is preferably recycled via conduits 888 and 832 to the water-rich section of column 850, so as to recover additional quantities of ethylene oxide present in this stream. The vapors obtained from separator 852 which are rich in $CO_2$, are withdrawn therefrom via conduit 890 and are passed to reabsorber 810 via conduit 812 to reabsorb any ethylene oxide remaining in these vapors, with the unabsorbed gases being vented, as described previously, via conduit 814. Alternatively, as when the ethylene oxide content of the vapors withdrawn from separator 852 is sufficiently low (e.g., by use of a water wash step), the vapors in conduit 890 may be vented directly to the atmosphere.

Distillation zone 265 will generally comprise at least 2 theoretical vapor-liquid contacting stages, preferably from 5 to 20, and more preferably from 8 to 15, theoretical vapor-liquid contacting stages.

The quantity of heat introduced to aldehyde removal column 850 via conduit 862 is preferably at least about 5 percent, preferably from about 10 to 70 percent, most preferably from about 25 to 50 percent, of the "total stripping heat" supplied to column 850, i.e., the sum of the sensible and latent heat introduced to column 850 via conduits 858 and 862.

The operating conditions used in column 264 will vary widely, depending on such factors as the composition of the liquid passed thereto via conduit 262, the degree of removal desired therein of dissolved carbon dioxide and other factors which will be apparent to the skilled practitioner. Generally, however, column 264 employs a bottoms temperature of from about 30 to 80° C., and usually from about 40 to 60° C., and an overhead pressure of from about 25 to 100 psig, and usually from about 25 to 50 psig.

Figure 9:
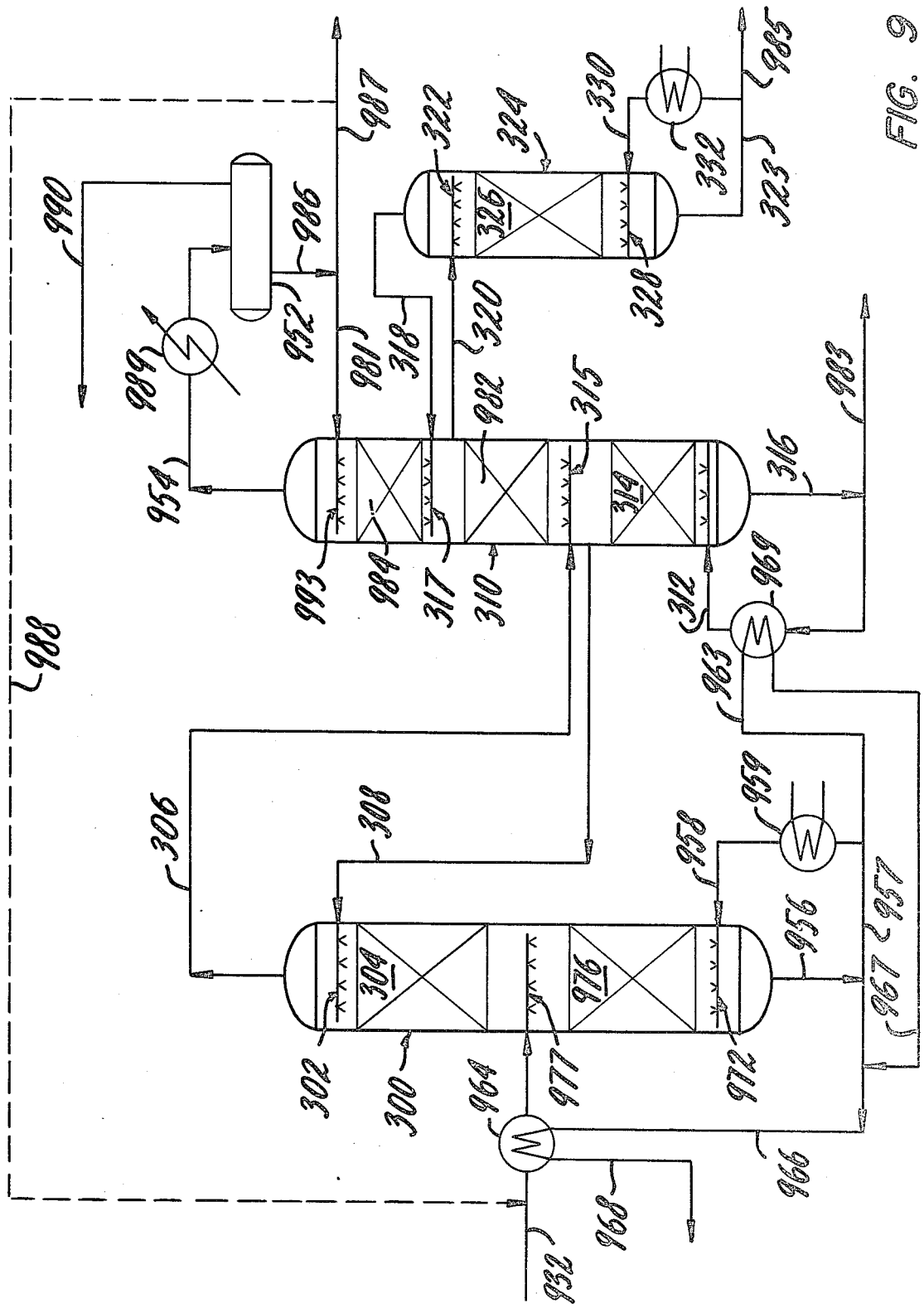
FIG. 9 is a diagrammatic illustration of a seventh embodiment of the process of the present invention in which the aldehyde removal columns of FIG. 7 are supplemented by addition of a sidestream stripping column (324) for removal of carbon dioxide.

FIG. 9 illustrates an embodiment of this invention in which the embodiment of FIG. 7 is supplemented by the addition of a sidestream stripper for removal of carbon dioxide passed to the first distillation column. As with the embodiment of FIG. 8, the embodiment illustrated in FIG. 9 will be particularly suitable in the treatment of an impure aqueous ethylene oxide liquid which contains high $CO_2$ concentrations. In FIG. 9, in which like elements of structure to the embodiments of FIGS. 2 to 4 employ the numerals of those figures preceded by the number "9", an impure aqueous ethylene oxide stream containing dissolved carbon dioxide is passed via conduit 932, heat exchanger 964 and distributing member 977 to first distillation column 300 in which is provided above the feed thereto distillation zone 304 and below the feed, distillation zone 976. Overhead vapors are withdrawn from column 300 via conduit 306 and passed via distributing member 315 to second distillation column 310 in which is provided above the feed, in ascending order, distillation zone 982 and 984, and below the feed, distillation zone 314. Bottoms product from column 300 is withdrawn via conduit 956, a portion of which bottoms are passed via conduit 966 to heat exchanger 964, with part of the bottoms also being recycled to column 300 via conduit 957, reboiler 959, conduit 958 and distributing member 972, as described previously. As with the previous embodiments, the cooled bottoms product withdrawn via conduit 968 from heat exchanger 964 is preferably recycled to a reabsorber (not shown) (e.g., via conduit 256 to reabsorber 810 in the embodiment of FIG. 8).

Overhead vapors produced in column 310 are withdrawn therefrom via conduit 954, condensed in condenser 989 and passed to vapor-liquid separator 952, from which separated liquid is withdrawn via conduit 986 and, in part, recycled to column 310 via conduit 981 and distributing member 993 as liquid reflux, with the remaining separated liquid being withdrawn via conduit 987 as the formaldehyde-rich ethylene oxide stream. As described with the previous embodiments, at least a portion of such withdrawn formaldehyde-rich stream is preferably recycled via conduit 988 and 932 to column 300. Vapors separated in separator 952 are preferably recycled via conduit 990, as described in the embodiment of FIG. 8, to a reabsorber (e.g., reabsorber 810 in the embodiment of FIG. 8), to provide for removal from the system via the overheads from the reabsorber of the high concentrations of carbon dioxide which will be contained in the overheads withdrawn from the second distillation column 310 via conduit 954.

Similarly to the embodiment of FIG. 8, the liquid introduced via conduit 932 to first distillation column 300 will contain large amounts of dissolved carbon dioxide. There is therefore also provided in this embodiment a conduit 320 by which at least a portion of the liquid downflowing from distillation zone 984 is withdrawn from second distillation column 320 and introduced to the upper portion of sidestream stripper 234 via distributing member 322. In stripper 324 there is provided distillation zone 326 in which the downflowing liquid so introduced is countercurrently contacted with upwardly flowing vapors which are introduced to stripper 324 by means of distributing member 328 and which result from the treatment from reboiler 332 of a portion of the stripper bottoms which are, in turn, withdrawn from stripper 324 via conduit 323. The remaining portion of bottoms withdrawn from stripper 324 is passed to conduit 985 and comprises the desired ethylene oxide-containing stream substantially free of aldehydic impurities and carbon dioxide.

Overhead product formed in stripper 324 is rich in carbon dioxide which has been stripped by treatment of the sidedraw in stripper 324 and is passed via conduit 318 and distributing member 317 as recycle to column 310, such recycle being introduced to column 310 at a point in the column below the distillation zone 984. As described previously, these carbon dioxide gases are withdrawn from column 310 with the vapors in conduit 954 and predominantly pass into conduit 990, and can be recycled to a reabsorber.

Distillation zone 976 in column 300 corresponds to distillation zone 76 in the embodiments of FIGS. 3 and 4 and has been described previously. As in FIG. 7, the distillation zone in column 300 above the feed thereto (zone 304 in FIG. 9) corresponds to first and second fractionation region 76 and 80 in FIGS. 3 and 4 and therefore possesses at least 2 theoretical vapor-liquid contacting stages and preferably from 2 to 35, more preferably from 4 to 16, and most preferably from about 6 to 11, theoretical vapor-liquid contacting stages. Similarly to FIG. 7, distillation zones 982 and 984 in column 310 correspond to distillation zones 82 and 84, respectively, of FIGS. 3 and 4 and therefore comprise the third and fourth fractionation region, respectively; the number of theoretical vapor-liquid contacting stages employed in distillation zone 682 and 684 therefore corresponds to that discussed above for zones 82 and 84.

Distillation zone 314 below the feed to column 310 comprises a sixth fractionation region, and therefore corresponds to distillation zone 218 of the embodiment of FIG. 6. Distillation zone 314 therefore possesses at least 1 theoretical vapor-liquid contacting stage, and preferably has from 2 to 50, more preferably from 5 to 30, and most preferably from 10 to 20 theoretical vapor-liquid contacting stages. Bottoms product is withdrawn from column 310 via conduit 316 and a portion thereof is recycled via reboiler 969 and conduit 312 to the lower portion of column 310. The remaining bottoms product is passed to conduit 983 and comprises the acetaldehyde-rich ethylene oxide stream. As in FIG. 7, the flow rate of the acetaldehyde-rich ethylene oxide stream (at steady state conditions) in conduit 985 of FIG. 9 is generally from about 0.1 to 10 percent of the flow rate of the ethylene oxide product stream which is withdrawn via conduit 985.

Distillation zone 326 in sidestream stripper 324 corresponds to distillation zone 265 in the embodiment of FIG. 8 and therefore generally comprises at least 2 theoretical vapor-liquid contacting stages, preferably from 5 to 20, and more preferably from 8 to 15 theoretical vapor-liquid contacting stages.

As described previously, the quantity of heat introduced to second distillation column 310 via conduit 312 is preferably at least about 5 percent, preferably from about 10 to 70 percent, most preferably from about 25 to 50 percent, of the "total stripping heat" supplied to columns 300 to 310, i.e., the sum of the sensible and latent heat introduced to columns 300 and 310 via conduits 958 and 312.

The general composition of the impure liquid passed to column 300 via conduit 932 corresponds to that discussed previously for the impure liquid fed to aldehyde removal column 850 in FIG. 8, and the operating conditions of sidestream stripper 324 correspond to that discussed above for column 264 in FIG. 8.

The amount of liquid reflux introduced to column 310 via conduit 981 is sufficient to provide an internal liquid reflux ratio of at least 1.35:1, and preferably from about 1.35:1 to 10:1, more preferably from 3.5:1 to 7.5:1, and most preferably from about 4:1 to 6:1, the internal liquid reflux being defined by the expression (I) above having reference to the zones and streams defined for FIG. 9.

As shown in U.S. Pat. No. 3,904,656 referred to above, the prior art ethylene oxide process also contemplates passing a portion of the reabsorbate (e.g., reabsorbate in line 16 of FIG. 1 above) to a conventional ethylene glycol process wherein the ethylene oxide content of the reabsorbate is reacted in an ethylene glycol reactor with water to form glycol derivatives of the epoxide. When the ethylene glycol process employs a stripping column prior to the ethylene glycol reactor to treat the reabsorbate to remove $CO_2$ and other dissolved gases prior to the reactor, it will be understood that liquid effluent from such column can be passed to an aldehyde removal column 50 (e.g., via line 32 in FIG. 2) for obtention of a purified ethylene oxide stream in accordance with the process of this invention. Thus, it will be understood that column 30 in FIG. 2 can comprise the glycol reactor feed stripper.

The invention will be more fully understood by reference to the following specific examples, but it is to be understood that these examples are given solely for illustrative purposes and are not intended to be limitative of the invention. In the examples that follow, and throughout the specification, parts are by weight unless otherwise indicated.

EXAMPLE 1

An impure aqueous ethylene oxide solution substantially free of carbon dioxide is continuously processed in a multi-stage, countercurrent distillation column similar to that depicted in FIG. 4. The column, having reference to the reference numerals employed in FIG. 4, contains 3 theoretical vapor-liquid contacting stages in zone 78, 2 theoretical vapor-liquid contacting stages in zone 80, 38 theoretical vapor-liquid contacting stages in zone 82, 4 theoretical vapor-liquid contacting stages in zone 84 and 7 theoretical vapor-liquid contacting stages in zone 76. Temperatures, flow rates, sensible heat content and composition of the various streams are given in Table I. The reference numberals appearing in parenthesis below the stream identifications are those used in FIG. 4 and are provided to facilitate a cross-reference between this example and the drawing. The internal liquid reflux employed is 6.0:1, as determined by expression (I) above.

From the foregoing it will be appreciated that the stripping vapor introduced to the various columns of FIGS. 5 through 9 can also comprise steam or other suitable inert heating fluid in addition to, or instead of, the indicated recycles of bottoms product and side streams, in the Figures indicated.

FIG. 5 — column 205, conduit 558 and column 206, conduit 562;

FIG. 6 — column 210, conduit 658 and column 212, conduit 226;

FIG. 7 — column 286, conduit 758 and column 287, conduit 289;

FIG. 8 — column 850, conduits 858 and 862 and column 264, conduit 272; and

FIG. 9 — column 300 (conduit 958), column 310 (conduit 312), and column 324 (conduit 330).

It will be obvious that various changes and modifications may be made without departing from the invention and it is intended, therefore, that all mater contained in the foregoing description shall be interpreted as illustrative only and not limitative of the invention.

I claim:

1. A process for treating impure aqueous ethylene oxide solutions containing as impurity at least one aldehyde selected from the group consisting of formaldehyde and acetaldehyde to provide ethylene oxide substantially free of said aldehydic impurities and water is provided which comprises (a) passing said impure solution as a feed stream to a multi-stage countercurrent distillation zone having disposed therewithin in ascending order above said feed stream the following fractionation regions:

(1) a first fractionation region of at least 1 theoretical vapor-liquid contacting stage;

(2) a second fractionation region of at least 1 theoretical vapor-liquid contacting stage;

TABLE I

| Stream | Feed (32) | Bottoms Product (68) | Bottoms Recycle (58) | Side-Stream Recycle (62) | CH$_3$CHO—rich E. O. Stream (83) | E. O. Product Stream (85) | Overh'd Vapor (54) | Reflux (81) | HCHO—rich E. O. Stream (87) |
|---|---|---|---|---|---|---|---|---|---|
| Temp., °C | 53 | 65 | 146 | 56 | 52 | 48 | 48 | 47 | 47 |
| Press., kg/cm$^2$, abs. | — | — | 4.3 | 4.0 | 4.0 | 3.7 | 3.7 | 3.7 | 3.7 |
| Flow, kg/hour | 14,822 | 13,088 | — | — | 262 | 1,310 | 9,570 | 9,408 | 162 |
| Heat input/output 10$^6$ kcal | — | — | 1.28 in | 0.51 in | — | — | 1.25 out | — | — |
| Composition, wt% | | | | | | | | | |
| Ethylene Oxide (E.O.)* | 11.9 | 12ppm | 12ppm | 79.6 | 99.4 | 99.99 | 99.9 | 99.9 | 99.9 |
| Water | 86.9 | 98.4 | 98.4 | 20.0 | 0.6 | <0.01 | <0.01 | <0.01 | <0.01 |
| Ethylene Glycol | 1.06 | 1.6 | 1.6 | 0.01 | nil | nil | nil | nil | nil |
| Formaldehyde* | .0050 | .0053 | .0053 | 4 ppm | 3.5ppm | 3.4ppm | 0.030 | 0.030 | 0.030 |
| Acetaldehyde* | .0050 | — | — | 0.40 | 0.28 | 5 ppm | 5 ppm | 5 ppm | 5ppm |

*Expressed as parts per million (ppm), where indicated, not weight percent.

EXAMPLE 2

The process of Example 1 is repeated except that no sidestream injection of stripping vapor is employed so that the stripping vapor is introduced only via conduit 58. The data thereby obtained are set forth in Table II below.

TABLE II

| Stream | Feed (32) | Bottoms Product (56) | Bottoms Recycle (58) | CH$_3$CHO—rich E. O. Stream (83) | E. O. Product Stream (85) | Overh'd Vapor (54) | Reflux (81) | HCHO—rich E. O. Stream (87) |
|---|---|---|---|---|---|---|---|---|
| Temp., °C | 53 | 65 | 146 | 52 | 48 | 48 | 47 | 47 |
| Press., kg/cm$^2$, abs. | — | — | 4.3 | 4.0 | 3.7 | 3.7 | 3.7 | 3.7 |
| Flow, kg/hour | 14,822 | 13,088 | — | 262 | 1,027 | 9,570 | 9,126 | 444 |
| Heat input/output 10$^6$ | — | — | 1.79in | — | — | 1.25ount | — | — |
| Composition, wt% | | | | | | | | |
| Ethylene Oxide (E. O.)* | 11.9 | 12 ppm | 12 ppm | 99.4 | 99.99 | 99.9 | 99.9 | 99.9 |
| Water | 86.9 | 98.4 | 98.4 | 0.6 | <0.01 | <0.01 | <0.01 | <0.01 |
| Ethylene Glycol | 1.06 | 1.6 | 1.6 | nil | nil | nil | nil | nil |
| Formaldehyde* | 0.005 | 0.0046 | 0.0046 | 8.5 ppm | 8.5 ppm | 0.03 | 0.03 | 0.03 |
| Acetaldehyde* | 0.005 | — | — | 0.28 | 5ppm | 5ppm | 5ppm | 5ppm |

*Expressed as parts per million (ppm), where indicated, not weight percent.

(3) a third fractionation region of at least 5 theoretical vapor-liquid contacting stages; and
(4) a fourth fractionation region of at least 1 theoretical vapor-liquid contacting stage; said multistage, countercurrent distillation zone having disposed therewithin below said feed stream a fifth fractionation region of at least 1 theoretical vapor-liquid contacting stage; each of said fractionation regions having means for providing countercurrent contact between downflowing liquid and upwardly flowing vapor;
(b) introducing stripping vapor to said distillation zone below said fifth fractionation region;
(c) withdrawing from the distillation zone as a first side stream at least a portion of the liquid downflowing from said third fractionation region, said first side stream comprising an acetaldehyde-rich ethylene oxide stream;
(d) withdrawing from the distillation zone as a second side stream at least a portion of the liquid downflowing from said fourth fractionation region, said second side stream comprising ethylene oxide substantially free of aldehydic impurities and water;
(e) withdrawing formaldehyde-containing vapor from said distillation zone above said fourth fractionation region, condensing at least a portion of said withdrawn vapor and recycling at least a portion of the condensate so produced as liquid reflux to the distillation zone above said fourth fractionation region; said condensate being recycled as reflux to said distillation zone in an amount sufficient to provide an internal liquid reflux ratio of at least about 1.35:1, as defined by the expression $$R = L/P+F$$

wherein R is the internal liquid reflux ratio, L is the moles per hour of liquid downflowing to the third fractionation region from the fourth fractionation region, P is the moles per hour of liquid withdrawn as said second side stream and F is the moles per hour of said withdrawn vapor not so recycled as condensate to the distillation zone; the portion of said condensate not so recycled being withdrawn as a formaldehyde-rich, ethylene oxide stream; and
(f) withdrawing from the distillation zone a liquid bottoms product comprising an aqueous solution substantially free of ethylene oxide.

2. The process of claim 1 wherein at least a portion of liquid downflowing from said second fractionation region is withdrawn from the distillation zone as a third side stream, and the withdrawn third side stream is at least partially vaporized and reintroduced as a source of side-stream vapor to the distillation zone between said first and second fractionation regions; the quality of heat introduced to the distillation zone with said side-stream vapor comprising at least 5% of the total stripping heat supplied to the distillation zone.

3. The process according to claim 2 wherein the quantity of heat introduced to the distillation zone with said side-stream vapor comprises from about 10 to 70 percent of the total stripping heat supplied to the distillation zone.

4. The process of claim 1 wherein side-stream stripping vapor is introduced to the distillation zone between said first and second fractionation regions, the quantity of heat introduced to the distillation zone with said side-stream stripping vapor comprising at least 5% of the total stripping heat supplied to the distillation zone.

5. The process according to claim 4 wherein the quantity of heat introduced to the distillation zone with said side-stream stripping vapor comprises from about 10 to 70% of the total stripping heat supplied to the distillation zone.

6. The process according to claim 1 wherein said second side stream contains less than about 10 parts by weight of aldehydic impurities per one million parts by weight of said second side stream.

7. The process according to claim 1 wherein the internal liquid reflux ratio is from about 1.35:1 to 10:1.

8. The process according to claim 1 wherein said first fractionation region possesses from 1 to 20 theoretical vapor-liquid contacting stages.

9. The process according to claim 1 wherein the second fractionation region possesses from 1 to 35 theoretical vapor-liquid contacting stages.

10. The process of claim 1 wherein the third fractionation region possesses from 10 to 60 theoretical vapor-liquid contacting stages.

11. The process of claim 1 wherein the fourth fractionation region possesses from 1 to 20 theoretical vapor-liquid contacting stages.

12. The process of claim 1 wherein the fifth fractionation region possesses from 1 to 20 theoretical vapor-liquid contacting stages.

13. The process according to claim 1 wherein the impure aqueous ethylene oxide solution contains dissolved carbon dioxide and wherein said second side stream withdrawn in step (d) is passed to a second distillation zone of at least two theoretical vapor-liquid contacting stages wherein the second side stream is treated for removal of dissolved carbon dioxide, thereby producing a bottoms product comprising ethylene oxide substantially free of aldehydic impurities, water, and carbon dioxide and an overhead product comprising carbon dioxide vapors, said overhead product being reintroduced to said multi-stage countercurrent distillation zone below said fourth fractionation region.

14. The process of claim 1 wherein said first side stream withdrawn from said multi-stage distillation zone is passed as feed to the upper portion of a sidestream distillation zone having disposed therewithin a sixth fractionation region of at least 1 theoretical vapor-liquid contacting stage, in which said sidestream is countercurrently contacted with upwardly flowing stripping vapor introduced to the lower portion of said sidestream distillation zone, to form (1) overhead vapors which are introduced to said multi-stage distillation zone below said third fractionation region, and (2) a bottoms product comprising said acetaldehyde-rich ethylene oxide stream.

15. The process according to claim 14 in which at least a portion of the bottoms product withdrawn from the sidestream distillation zone is vaporized to form the stripping vapors introduced to said sidestream distillation zone; the quantity of heat introduced to the sidestream distillation zone with said vapor comprising at least 5% of the total stripping heat supplied to said multi-stage fractionation zone and said sidestream distillation zone.

16. The process according to claim 14 in which said sixth fractionation region possesses from 2 to 35 theoretical vapor-liquid contacting stages.

17. A process for treating impure aqueous ethylene oxide solutions containing as impurity at least one aldehyde selected from the group consisting of formaldehyde and acetaldehyde to provide ethylene oxide substantially free of said aldehydic impurities and water, is provided which comprises (a) passing said impure solution as a feed stream to a first multi-stage countercurrent distillation zone having disposed therewithin above said feed stream a first fractionation region of at least one theoretical vapor-liquid contacting stage and having disposed therewithin below said feed stream a second fractionation region of at least one theoretical vapor-liquid contacting stage;

(b) introducing stripping vapor to said first distillation zone below said second fractionation region;

(c) withdrawing from the upper portion of said first distillation zone a first overhead product and introducing said first overhead product as feed to the lower portion of a second multi-stage countercurrent distillation zone, said second distillation zone having disposed therewithin above the feed stream thereto the following fractionation regions;
  (1) a third fractionation region of at least one theoretical vapor-liquid contacting stage;
  (2) a fourth fractionation region of at least five theoretical vapor-liquid contacting stages; and
  (3) a fifth fractionation region of at least one theoretical vapor-liquid contacting stage;

(d) withdrawing from the lower portion of said second countercurrent distillation zone first bottoms product and introducing said first bottoms product to the upper portion of said first countercurrent distillation zone above said first fractionation region;

(e) withdrawing second bottoms product from the lower portion of said first distillation zone, said second bottoms product comprising an aqueous solution substantially free of ethylene oxide;

(f) withdrawing from said second distillation zone as a first side stream at least a portion of the liquid downflowing from said fourth fractionation region, said first sidestream comprising an acetaldehyde-rich ethylene oxide stream;

(g) withdrawing from the second distillation zone as a second sidestream at least a portion of the liquid downflowing from said fifth fractionation region, said second sidestream comprising ethylene oxide substantially free of aldehydic impurities and water; and (h) withdrawing formaldehyde-containing vapor from said distillation zone above said fifth fractionation region, condensing at least a portion of said withdrawn vapor and recycling at least a portion of the condensate so produced as liquid reflux to the distillation zone above said fifth fractionation region; said condensate being recycled as reflux to said distillation zone in an amount sufficient to provide an internal liquid reflux ratio of at least about 1.35:1, as defined by the expression $$R = L/P+F$$

wherein R is the internal liquid reflux ratio, L is the moles per hour of liquid downflowing to the fourth fractionation region from the fifth fractionation region, P is the moles per hour of liquid withdrawn as said second side stream and F is the moles per hour of said withdrawn vapor not so recycled as condensate to the second distillation zone; the portion of said condensate not so recycled being withdrawn as a formaldehyde-rich, ethylene oxide stream.

18. A process for treating impure aqueous ethylene oxide solutions containing as impurity at least one aldehyde selected from the group consisting of formaldehyde and acetaldehyde to provide ethylene oxide substantially free of said aldehydic impurities and water, is provided which comprises:

(a) passing said impure solution as a feed stream to a first multi-stage countercurrent distillation zone having disposed therewithin in ascending order above said feed stream a first fractionation region of at least 1 theoretical vapor-liquid contacting stage and a second fractionation region of at least 1 theoretical vapor-liquid contacting stage; and having disposed therewithin below said feed stream a third fractionation region of at least 1 theoretical vapor-liquid contacting stage; each of said fractionation regions having means for providing countercurrent contact between downflowing liquid and upwardly flowing vapor;

(b) introducing stripping vapor to said distillation zone below said third fractionation region;

(c) withdrawing overhead product from said first distillation zone and introducing said overhead product as feed to a second multi-stage countercurrent distillation zone, said second zone having disposed therewithin in ascending order above said feed stream the following fractionation regions:
  (1) a fourth fractionation region of at least 5 theoretical vapor-liquid contacting stages; and
  (2) a fifth fraction region of at least 1 theoretical vapor-liquid contacting stage; and having disposed therewithin below said feed stream a sixth fractionation region of at least 1 theoretical vapor-liquid contacting stage; each of said fractionation regions having means for providing countercurrent contact between downflowing liquid and upwardly flowing vapor;

(d) introducing stripping vapor to said distillation zone below said sixth fractionation region;

(e) withdrawing from the second distillation zone at least a portion of the liquid downflowing from said fourth fractionation region, and recycling said withdrawn liquid as reflux to the upper portion of said first distillation zone above said second fractionation region;

(f) withdrawing from the second distillation zone at least a portion of the liquid downflowing from the fifth fraction region, said withdrawn liquid comprising ethylene oxide product substantially free of aldehydic impurities and water;

(g) withdrawing bottoms product from the second distillation zone said withdrawn bottoms product comprising an acetaldehyde-rich ethylene oxide stream; and (h) withdrawing formaldehyde-containing vapor from said second distillation zone above said fifth fractionation region, condensing at least a portion of said withdrawn vapor and recycling at least a portion of the condensate so produced as liquid reflux to the second distillation zone above said fifth fractionation region; said condensate being recycled as reflux to said second distillation zone in an amount sufficient to provide an internal liquid reflux ratio of at least about 1.35:1, as defined by the expression $$R = L/P+F$$

wherein R is the internal liquid reflux ratio, L is the moles per hour of liquid downflowing to the fourth fractionation region from the fifth fractionation region, P is the moles per hour of liquid withdrawn as the ethylene oxide product stream and F is the moles per hour of said withdrawn vapor not so recycled as condensate to the second distillation zone; the portion of said condensate not so recycled being withdrawn as a formaldehyde-rich, ethylene oxide stream.

19. The process according to claim 18 wherein at least a portion of the bottoms product withdrawn from the second distillation zone is partially vaporized in a vaporizing zone and recycled to the second distillation zone as said stripping vapor in an amount sufficient to provide at least 5% of the total stripping heat supplied to the first and second distillation zones.

20. The process according to claim 18 wherein at least a portion of the bottoms product withdrawn from the second distillation zone is partially vaporized in a vaporizing zone and recycled to the second distillation zone as said stripping vapor in an amount sufficient to provide from about 10 to 70 percent of the total stripping heat supplied to the first and second distillation zones.

21. The process of claim 18 wherein sidestream stripping vapor is introduced to the distillation zone between said first and second fractionation regions, the quantity of heat introduced to the distillation zone with said sidestream stripping vapor comprising at least 5% of the total stripping heat supplied to the distillation zone.

22. The process according to claim 18 wherein the quantity of heat introduced to the distillation zone with said sidestream stripping vapor comprises from about 10 to 70% of the total stripping heat supplied to the distillation zone.

23. The process according to claim 18 wherein said ethylene oxide product stream contains less than about 70 parts by weight of aldehydic impurities per one million parts by weight of said product stream.

24. The process according to claim 18 wherein R is from about 1.35:1 to 10:1.

25. The process according to claim 18 wherein the second fractionation region possesses from 1 to 20 theoretical vapor-liquid contacting stages.

26. The process according to claim 18 wherein the second fractionation region possesses from 1 to 15 theoretical vapor-liquid contacting stages.

27. The process of claim 18 wherein the third fractionation region possesses from 1 to 20 theoretical contacting stages.

28. The process of claim 18 wherein the fourth fractionation region possesses from 10 to 60 theoretical vapor-liquid contacting stages.

29. The process of claim 18 wherein the fifth fractionation region possesses from 1 to 20 theoretical vapor-liquid contacting stages.

30. The process according to claim 18 in which said sixth fractionation region possesses from 2 to 35 theoretical vapor-liquid contacting stages.

31. The process according to claim 18 wherein the impure aqueous ethylene oxide solution contains dissolved carbon dioxide and wherein at least a portion of liquid downflowing from the fifth fractionation region is withdrawn from said second distillation zone and is passed to the upper portion of a third distillation zone wherein the withdrawn liquid is treated for removal as overhead of dissolved carbon dioxide, thereby producing a bottoms product comprising ethylene oxide substantially free of aldehydic impurities, water and carbon dioxide and an overhead product comprising carbon dioxide vapors, said overhead product being reintroduced to the second distillation zone below said fifth fractionation region.

* * * * *

UNITED STATES PATENT AND TRADEMARK OFFICE
CERTIFICATE OF CORRECTION

PATENT NO. : 4,134,797  Page 1 of 2
DATED : Jan. 16, 1979
INVENTOR(S) : Brian J. Ozero It is certified that error appears in the above—identified patent and that said Letters Patent is hereby corrected as shown below:

Col. 2, line 37 - "therewith" should be --therewithin--

Col. 8, line 15 - "practioner" should be --practitioner--

Col. 10, line 24 - "i" should be --in--

Col. 11, line 11 - there should be only one "of"

Col. 13, line 15 - "121" should be --212--

Col. 14, line 8 - "538" should be --583--

Col. 15, line 36-37 - "corrresponds" should be --corresponds--

Col. 19, line 35 - "320" should be --310--

Col. 19, line 36 - "234" should be --324--

Col. 21, line 24 - "numberals" should be --numerals--

Col. 22, Table I - in the headings, "HCHO-" should be part of the last heading only Col. 21, Table II - "$10^6$" should be --$10^6$ kcal-- and, in the preceding line, "1.25ount" should be --1.25out--

UNITED STATES PATENT AND TRADEMARK OFFICE
CERTIFICATE OF CORRECTION

PATENT NO. : 4,134,797

DATED : Jan. 16, 1979

INVENTOR(S) : Brian J. Ozero

It is certified that error appears in the above—identified patent and that said Letters Patent is hereby corrected as shown below:

Col. 22, line 19 - "mater" should be --matter--

Col. 26, line 33 - "fraction" should be --fractionation--

Col. 26, line 51 - "fraction" should be --fractionation--

Signed and Sealed this

Twelfth Day of January 1982

[SEAL]

Attest:

GERALD J. MOSSINGHOFF

*Attesting Officer*     *Commissioner of Patents and Trademarks*